(12) United States Patent
Wilkinson

(10) Patent No.: US 11,039,843 B2
(45) Date of Patent: Jun. 22, 2021

(54) ALIGNMENT DEVICES AND METHODS

(71) Applicant: Smith & Nephew, Inc., Memphis, TN (US)

(72) Inventor: Zachary Christopher Wilkinson, Germantown, TN (US)

(73) Assignee: Smith & Nephew, Inc., Memphis, TN (US)

( * ) Notice: Subject to any disclaimer, the term of this patent is extended or adjusted under 35 U.S.C. 154(b) by 251 days.

(21) Appl. No.: 16/228,272

(22) Filed: Dec. 20, 2018

(65) Prior Publication Data
US 2019/0117235 A1  Apr. 25, 2019

Related U.S. Application Data

(62) Division of application No. 14/433,866, filed as application No. PCT/US2013/065730 on Oct. 18, 2013, now Pat. No. 10,499,933.

(Continued)

(51) Int. Cl.
| | |
|---|---|
| *A61B 17/17* | (2006.01) |
| *A61B 17/15* | (2006.01) |
| *A61F 2/46* | (2006.01) |
| *A61B 34/10* | (2016.01) |
| *A61F 2/38* | (2006.01) |

(Continued)

(52) U.S. Cl.
CPC .......... *A61B 17/175* (2013.01); *A61B 17/155* (2013.01); *A61B 17/1703* (2013.01); *A61B 17/1764* (2013.01); *A61B 34/10* (2016.02); *A61F 2/4657* (2013.01); *A61F 2/4684* (2013.01); *A61B 2017/00526* (2013.01); *A61B 2017/568* (2013.01); *A61B 2034/101* (2016.02); *A61B 2034/108* (2016.02); *A61F 2/389* (2013.01); *A61F 2/3859* (2013.01); *A61F 2002/4658* (2013.01); *A61F 2002/4668* (2013.01); *Y10T 29/49* (2015.01)

(58) Field of Classification Search
CPC .................................................. A61B 17/1764
See application file for complete search history.

(56) References Cited

U.S. PATENT DOCUMENTS

| | | |
|---|---|---|
| 3,798,679 A | 3/1974 | Ewald |
| 3,816,855 A | 6/1974 | Saleh |

(Continued)

FOREIGN PATENT DOCUMENTS

| | | |
|---|---|---|
| CN | 101415371 A1 | 4/2009 |
| CN | 101790353 A1 | 7/2010 |

(Continued)

OTHER PUBLICATIONS

Chinese Patent Application No. 201380066482.4 First Office Action dated Mar. 14, 2016.

(Continued)

*Primary Examiner* — Samuel S Hanna
(74) *Attorney, Agent, or Firm* — Troutman Pepper Hamilton Sanders LLP

(57) ABSTRACT

Embodiments of the invention include devices and methods for implanting arthroplasty devices. Some embodiments include designs that allow for use of x-ray images as the only images used to fully and accurately preoperatively and intraoperatively size and align arthroplasty device components and prepare all necessary tissue.

17 Claims, 26 Drawing Sheets

Related U.S. Application Data

(60) Provisional application No. 61/715,631, filed on Oct. 18, 2012.

(51) Int. Cl.
*A61B 17/56* (2006.01)
*A61B 17/00* (2006.01)

(56) References Cited

U.S. PATENT DOCUMENTS

| | | |
|---|---|---|
| 3,869,731 A | 3/1975 | Waugh et al. |
| 4,081,866 A | 4/1978 | Upshaw et al. |
| 4,207,627 A | 6/1980 | Cloutier |
| 4,211,228 A | 7/1980 | Cloutier |
| 4,249,270 A | 2/1981 | Bahler et al. |
| 4,474,177 A | 10/1984 | Whiteside |
| 4,524,766 A | 6/1985 | Petersen |
| 4,568,348 A | 2/1986 | Johnson et al. |
| 4,586,933 A | 5/1986 | Shoji et al. |
| 4,653,488 A | 3/1987 | Kenna et al. |
| 4,703,751 A | 11/1987 | Pohl |
| 4,711,639 A | 12/1987 | Grundel |
| 4,717,774 A | 1/1988 | Narayan et al. |
| 4,722,330 A | 2/1988 | Russell et al. |
| 4,738,253 A | 4/1988 | Buechel et al. |
| 4,738,254 A | 4/1988 | Buechel et al. |
| 4,773,407 A | 9/1988 | Petersen |
| 4,787,383 A | 11/1988 | Kenna |
| 4,907,578 A | 3/1990 | Petersen |
| 4,926,847 A | 5/1990 | Luckman |
| 4,938,769 A | 7/1990 | Shaw |
| 4,950,298 A | 8/1990 | Gustilo et al. |
| 4,952,213 A | 8/1990 | Bowman et al. |
| 4,963,152 A | 10/1990 | Hofmann et al. |
| 4,979,949 A | 12/1990 | Matsen, II et al. |
| 5,002,545 A | 3/1991 | Whiteside et al. |
| 5,007,933 A | 4/1991 | Sidebotham et al. |
| 5,037,423 A | 8/1991 | Kenna |
| 5,053,037 A | 10/1991 | Lackey |
| 5,062,852 A | 11/1991 | Dorr et al. |
| 5,080,675 A | 1/1992 | Lawes et al. |
| 5,098,436 A | 3/1992 | Ferrante et al. |
| 5,122,144 A | 6/1992 | Bert et al. |
| 5,234,433 A | 8/1993 | Bert et al. |
| 5,236,432 A | 8/1993 | Matsen, III et al. |
| 5,282,803 A | 2/1994 | Lackey |
| 5,356,414 A | 10/1994 | Cohen et al. |
| 5,417,694 A | 5/1995 | Marik et al. |
| 5,451,228 A | 9/1995 | Johnson et al. |
| 5,462,549 A | 10/1995 | Glock |
| 5,470,354 A | 11/1995 | Hershberger et al. |
| 5,474,559 A | 12/1995 | Bertin et al. |
| 5,609,645 A | 3/1997 | Vinciguerra |
| 5,611,802 A | 3/1997 | Samuelson et al. |
| 5,628,749 A | 5/1997 | Vendrely et al. |
| 5,634,927 A | 6/1997 | Houston et al. |
| 5,667,511 A | 9/1997 | Vendrely et al. |
| 5,683,469 A | 11/1997 | Johnson et al. |
| 5,688,280 A | 11/1997 | Booth et al. |
| 5,690,637 A | 11/1997 | Wen et al. |
| 5,702,464 A | 12/1997 | Lackey |
| 5,709,689 A | 1/1998 | Ferrante et al. |
| 5,776,200 A | 7/1998 | Johnson et al. |
| 5,776,201 A | 7/1998 | Colleran et al. |
| 5,782,925 A | 7/1998 | Collazo et al. |
| 5,830,216 A | 11/1998 | Insall et al. |
| 5,908,424 A | 6/1999 | Bertin et al. |
| 5,916,220 A | 6/1999 | Masini |
| 6,059,788 A | 5/2000 | Katz |
| 6,258,095 B1 | 7/2001 | Lombardo et al. |
| 6,482,209 B1 | 11/2002 | Engh et al. |
| 6,569,202 B2 | 5/2003 | Whiteside |
| 6,575,980 B1 | 6/2003 | Robie et al. |
| 6,770,077 B2 | 8/2004 | Van Zile et al. |
| 7,695,520 B2 | 4/2010 | Metzger et al. |
| 7,850,698 B2 | 12/2010 | Straszheim-Morley et al. |
| 8,025,663 B2 | 9/2011 | Keeven et al. |
| 8,273,131 B2 | 9/2012 | Metzger et al. |
| 8,491,587 B2 | 7/2013 | McGovern et al. |
| 8,500,818 B2 | 8/2013 | Metzger et al. |
| 2001/0001121 A1 | 5/2001 | Lombardo |
| 2002/0055784 A1 | 5/2002 | Burstein et al. |
| 2002/0173852 A1 | 11/2002 | Felt et al. |
| 2003/0028196 A1 | 2/2003 | Bonutti |
| 2003/0130665 A1 | 7/2003 | Pinczewski et al. |
| 2004/0153066 A1 | 8/2004 | Coon et al. |
| 2004/0153162 A1 | 8/2004 | Sanford et al. |
| 2005/0010302 A1 | 1/2005 | Dietz et al. |
| 2005/0143746 A1 | 6/2005 | Steffenmeier et al. |
| 2005/0149041 A1 | 7/2005 | McGinley et al. |
| 2005/0154394 A1 | 7/2005 | Michalowicz |
| 2005/0177169 A1 | 8/2005 | Fisher et al. |
| 2006/0015109 A1 | 1/2006 | Haines |
| 2006/0015115 A1 | 1/2006 | Haines |
| 2006/0015116 A1 | 1/2006 | Haines |
| 2006/0015117 A1 | 1/2006 | Haines |
| 2006/0030944 A1 | 2/2006 | Haines |
| 2006/0036257 A1 | 2/2006 | Steffensmeier et al. |
| 2006/0189998 A1 | 8/2006 | Rasmussen |
| 2006/0200158 A1 | 9/2006 | Farling et al. |
| 2007/0078517 A1 | 4/2007 | Engh et al. |
| 2007/0219560 A1 | 9/2007 | Hodorek |
| 2007/0233139 A1 | 10/2007 | Metcalfe et al. |
| 2007/0233140 A1 | 10/2007 | Metzger et al. |
| 2007/0282451 A1 | 12/2007 | Metzger et al. |
| 2008/0058945 A1 | 3/2008 | Hajaj et al. |
| 2008/0119938 A1 | 5/2008 | Oh |
| 2008/0140212 A1 | 6/2008 | Metzger et al. |
| 2008/0161815 A1 | 7/2008 | Schoenfeld et al. |
| 2008/0188855 A1 | 8/2008 | Brown et al. |
| 2009/0043309 A1 | 2/2009 | Rasmussen |
| 2009/0043310 A1 | 2/2009 | Rasmussen |
| 2009/0087276 A1* | 4/2009 | Rose .................. A61B 17/155 |
| | | 409/79 |
| 2009/0112212 A1 | 4/2009 | Murray et al. |
| 2009/0125029 A1 | 5/2009 | Seo et al. |
| 2009/0222014 A1 | 9/2009 | Bojarski et al. |
| 2009/0264890 A1 | 10/2009 | Duggineni et al. |
| 2009/0307893 A1 | 12/2009 | Burdulis, Jr. |
| 2010/0010635 A1 | 1/2010 | Straszheim-Morley et al. |
| 2010/0016977 A1 | 1/2010 | Masini |
| 2010/0016980 A1 | 1/2010 | Donno et al. |
| 2010/0094301 A1 | 4/2010 | Dees, Jr. et al. |
| 2010/0160919 A1 | 6/2010 | Axelson et al. |
| 2010/0198224 A1 | 8/2010 | Metzger et al. |
| 2010/0280624 A1 | 11/2010 | Engh et al. |
| 2010/0305575 A1 | 12/2010 | Wilkinson et al. |
| 2010/0305711 A1 | 12/2010 | McKinnon et al. |
| 2010/0324692 A1 | 12/2010 | Uthgenannt et al. |
| 2010/0331848 A1 | 12/2010 | Smith et al. |
| 2010/0331991 A1 | 12/2010 | Wilkinson et al. |
| 2011/0015749 A1 | 1/2011 | Engh et al. |
| 2011/0029093 A1* | 2/2011 | Bojarski ............... A61F 2/3859 |
| | | 623/20.35 |
| 2011/0046735 A1 | 2/2011 | Metzger et al. |
| 2011/0087332 A1 | 4/2011 | Bojarski et al. |
| 2011/0245835 A1 | 10/2011 | Dodds |
| 2011/0264097 A1 | 10/2011 | Hodorek et al. |
| 2012/0035736 A1 | 2/2012 | O'Connor et al. |
| 2012/0209270 A1 | 8/2012 | Segina et al. |
| 2012/0316564 A1 | 12/2012 | Serbousek et al. |
| 2013/0006375 A1 | 1/2013 | Metzger et al. |
| 2013/0030538 A1 | 1/2013 | Metzger et al. |
| 2013/0184713 A1 | 7/2013 | Bojarski et al. |
| 2013/0261503 A1 | 10/2013 | Sherman et al. |
| 2014/0066720 A1 | 3/2014 | Wilkinson et al. |

FOREIGN PATENT DOCUMENTS

| | | |
|---|---|---|
| EP | 0121142 B1 | 10/1984 |
| EP | 0243109 B1 | 10/1987 |
| EP | 0327249 B1 | 8/1989 |
| EP | 0336774 B1 | 10/1989 |
| EP | 0337901 A1 | 10/1989 |

(56) References Cited

FOREIGN PATENT DOCUMENTS

| | | |
|---|---|---|
| EP | 0380451 A2 | 8/1990 |
| EP | 0555003 B1 | 8/1993 |
| EP | 1136045 A2 | 9/2001 |
| EP | 1862149 B1 | 12/2007 |
| EP | 2168537 B1 | 3/2010 |
| JP | 1011541 A | 1/1989 |
| JP | 02246971 A | 10/1990 |
| JP | 04297254 A | 10/1992 |
| WO | 1991010408 A1 | 7/1991 |
| WO | 1994009730 A1 | 5/1994 |
| WO | 1996001588 A1 | 1/1996 |
| WO | 1997029704 A1 | 8/1997 |
| WO | 2003059203 A1 | 7/2003 |
| WO | 2006088684 A1 | 8/2006 |
| WO | 2008030842 A2 | 3/2008 |
| WO | 2010006677 A1 | 1/2010 |
| WO | 2010138836 A2 | 12/2010 |
| WO | 2010138841 A2 | 12/2010 |
| WO | 2010138850 A2 | 12/2010 |
| WO | 2010138854 A2 | 12/2010 |
| WO | 2010138857 A2 | 12/2010 |
| WO | 2012051542 A2 | 4/2012 |

OTHER PUBLICATIONS

Chinese Patent Application No. 201380066482.4 Second Office Action dated Feb. 3, 2017.
European Patent Application No. 13846492.0 First Office Action dated Oct. 24, 2017.
International Search Report/Written Opinion for PCT/US2013/065730, dated Jan. 22, 2014.
International Preliminary Report on Patentability for International Application No. PCT/US2013/065730, dated Apr. 21, 2015.
International Preliminary Report on Patentability for International Application No. PCT/US2010/036632, dated Nov. 29, 2011.
International Preliminary Report on Patentability for International Application No. PCT/US201036617, dated Nov. 29, 2011.
International Preliminary Report on Patentability for International Application for PCT/US2010/036642, dated Nov. 29, 2011.
International Preliminary Report on Patentability for International Application No. PCT/US2010/036608, dated Nov. 29, 2011.
International Preliminary Report on Patentability for International Application No. PCT/US2010/036638, dated Nov. 29, 2011.
Notice of Allowance for U.S. Appl. No. 12/790,227, dated Jan. 8, 2014.
Office Action for U.S. Appl. No. 11/933,298, dated Dec. 2, 2010.
Office Action for U.S. Appl. No. 12/790,002, dated Oct. 19, 2012.
Office Action for U.S. Appl. No. 12/790,036, dated Nov. 6, 2012.
Office Action for U.S. Appl. No. 12/790,036, dated May 29, 2013.
Office Action for U.S. Appl. No. 12/790,137, dated Nov. 2, 2012.
Office Action for U.S. Appl. No. 12/790,137, dated Jun. 12, 2013.
Office Action for U.S. Appl. No. 12/790,137, dated Aug. 8, 2013.
Office Action for U.S. Appl. No. 12/790,227, dated Nov. 2, 2012.
Office Action for U.S. Appl. No. 12/790,227, dated Jun. 5, 2013.
Office Action for U.S. Appl. No. 12/790,227, dated Oct. 1, 2013.
Office Action for U.S. Appl. No. 12/790,312, dated Nov. 8, 2012.
Office Action for U.S. Appl. No. 12/790,312, dated Jun. 11, 2013.
Office Action for U.S. Appl. No. 12/790,312, dated Sep. 30, 2013.
Styker, TriathlonTM Knee System Design Rationale Surgical Instrumentation and Implants Knee Technology Designed for Natural Motion Brochure, 16 pages, 2004.
Crossett, L.S. et al., AMK Congruency Instrument System, Surgical Technique, published by DePuy, 1997, Bates No. DEP00004252-DEP00004267, 16 pages.
Desjardins, D. et al., Interax Operative Techniques, Interax, Bates No. DEP00004391-DEP00004411, 21 pages.
Whiteside Ortholoc Total Knee System, Dow Corning Wright, pp. ZH0001 09679-ZH0001 09690, 12 pages.
Office Action for U.S. Appl. No. 14/057,824, dated Dec. 8, 2015.

\* cited by examiner

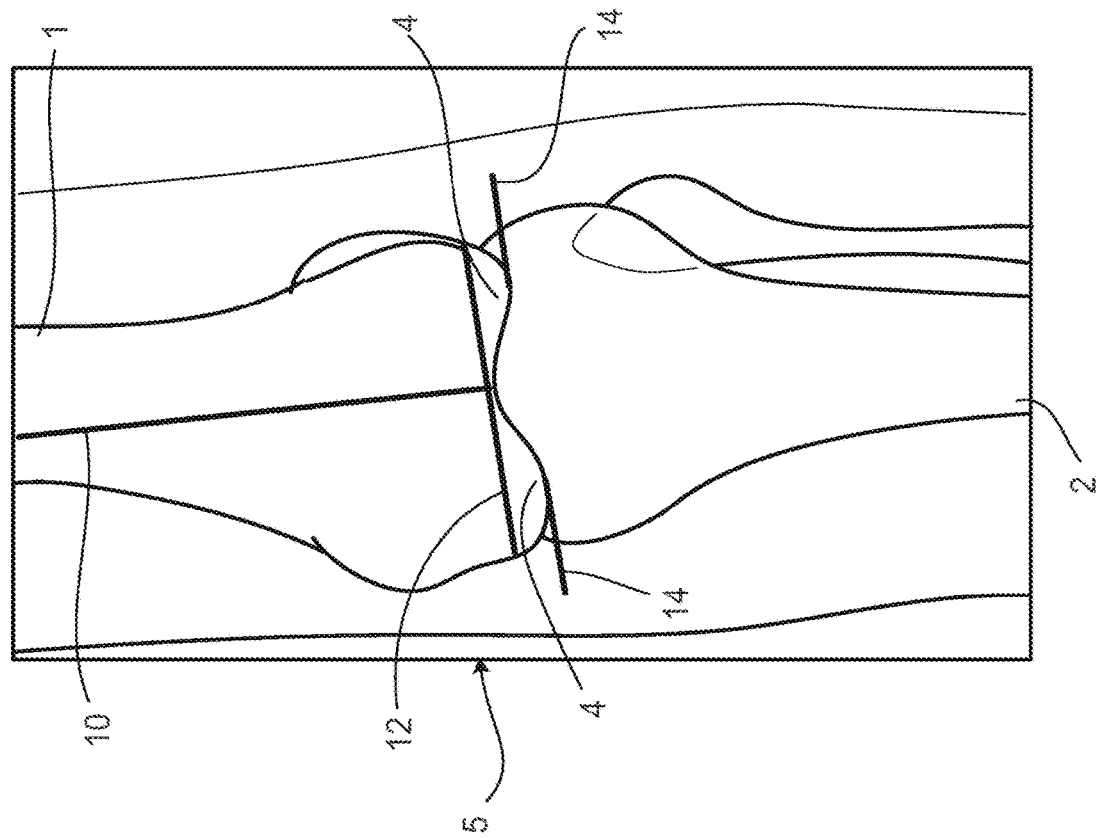
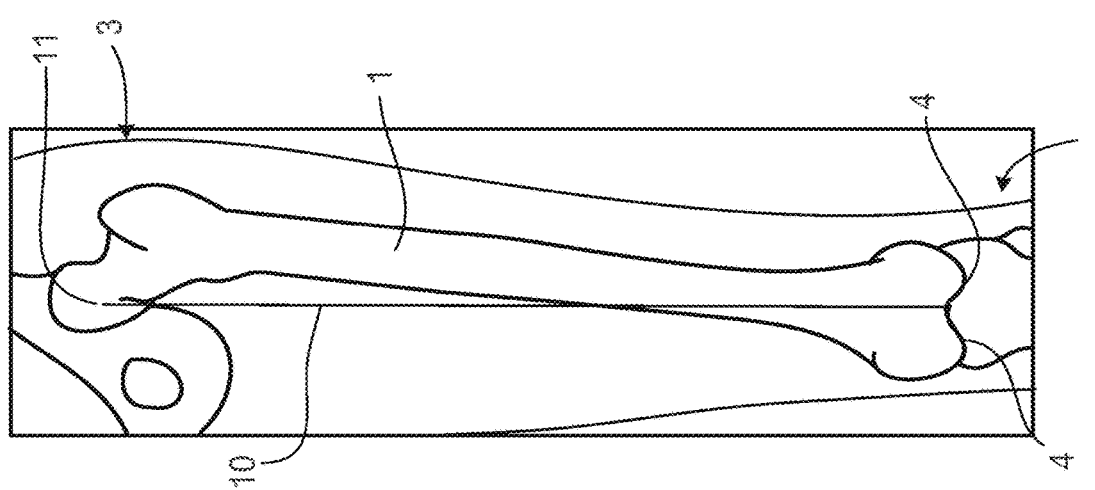

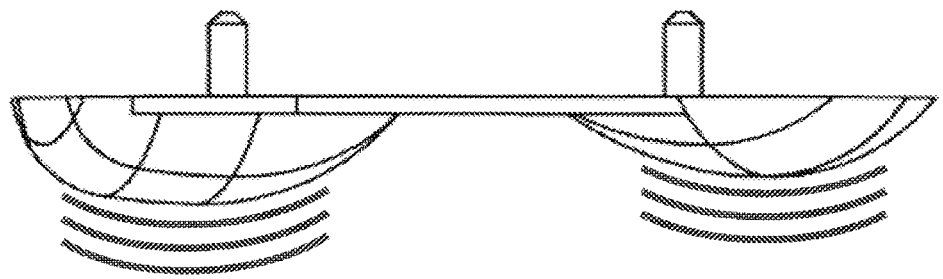
FIG. 15B
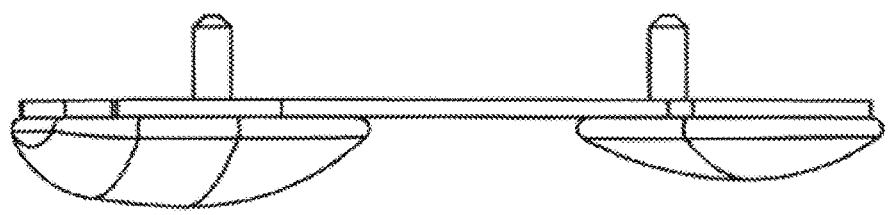
FIG. 15C
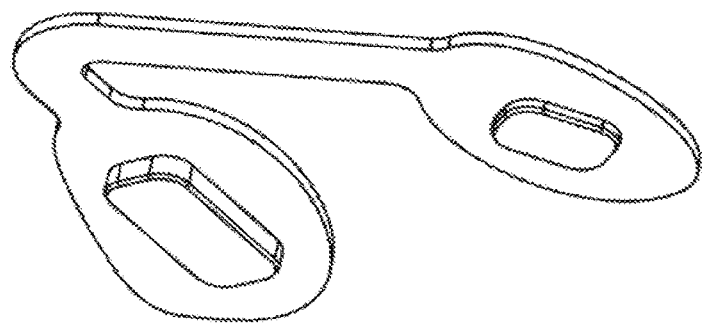
FIG. 15D
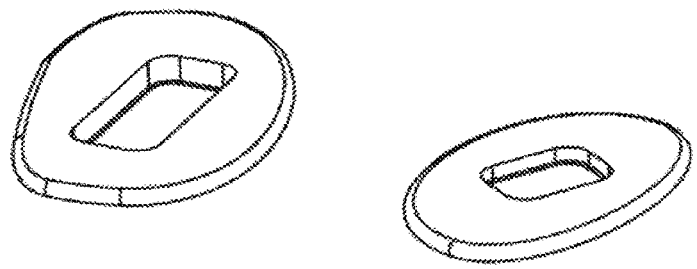

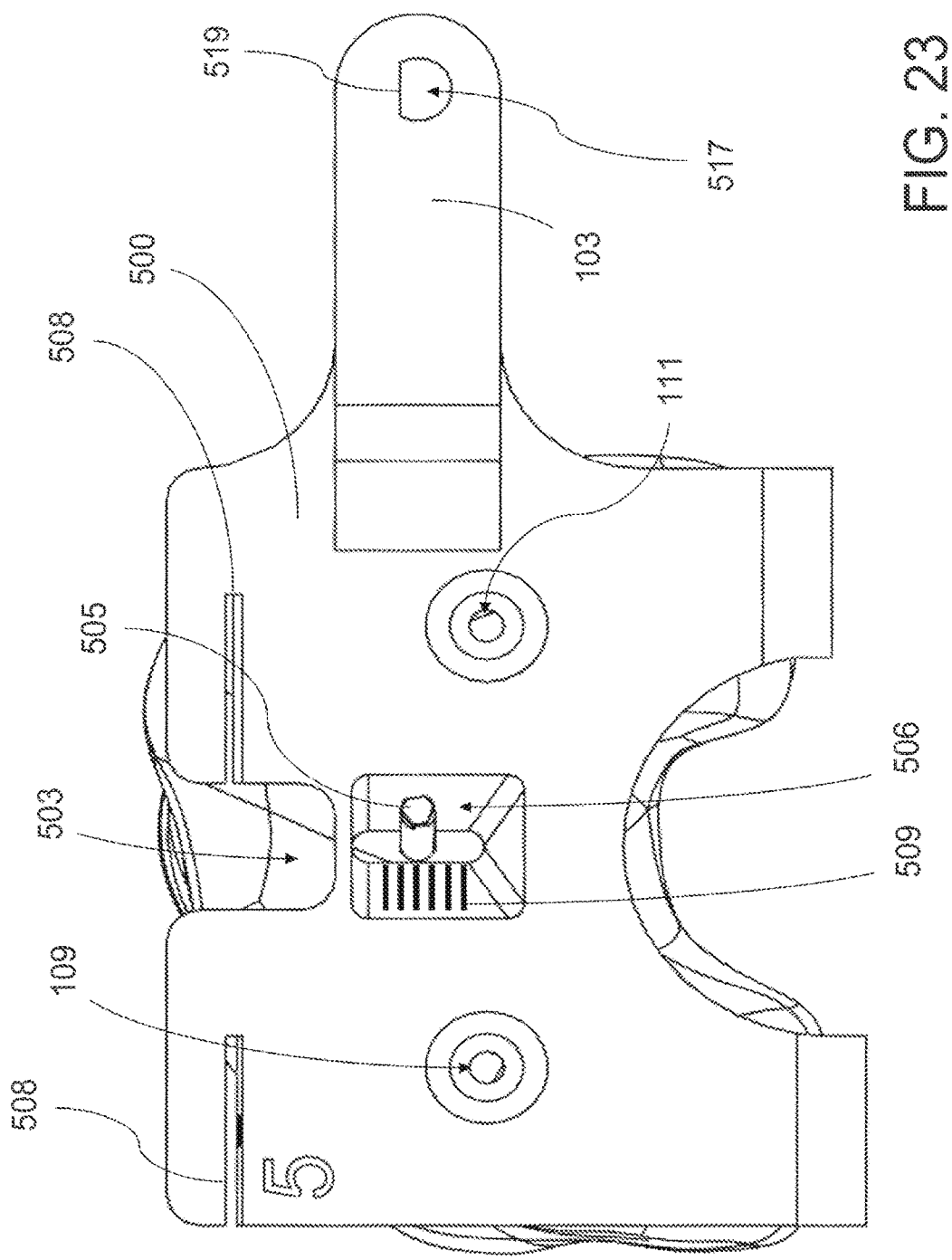

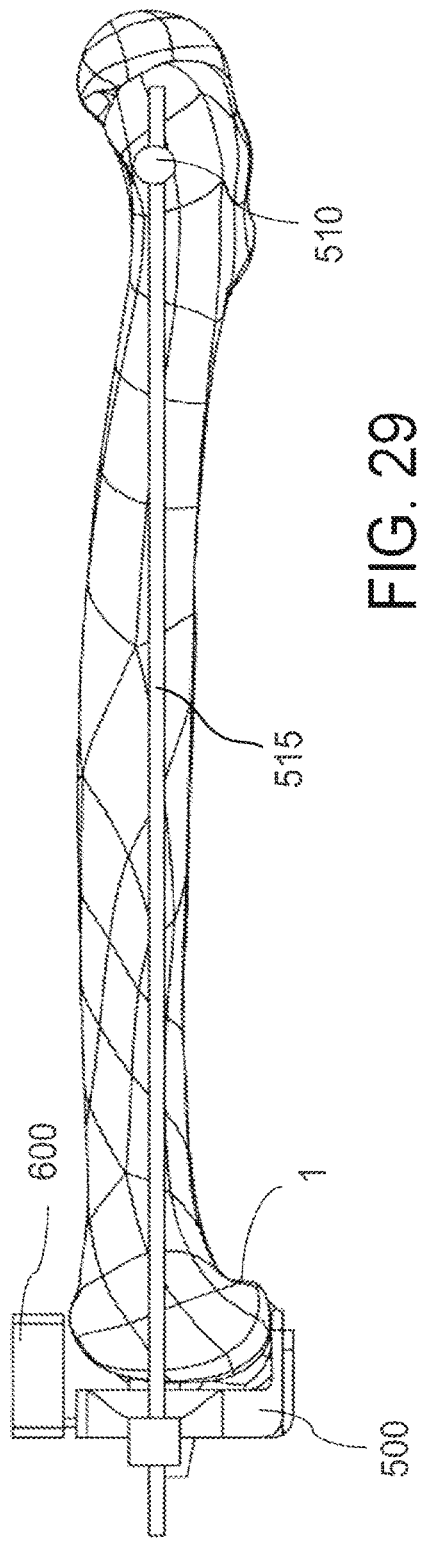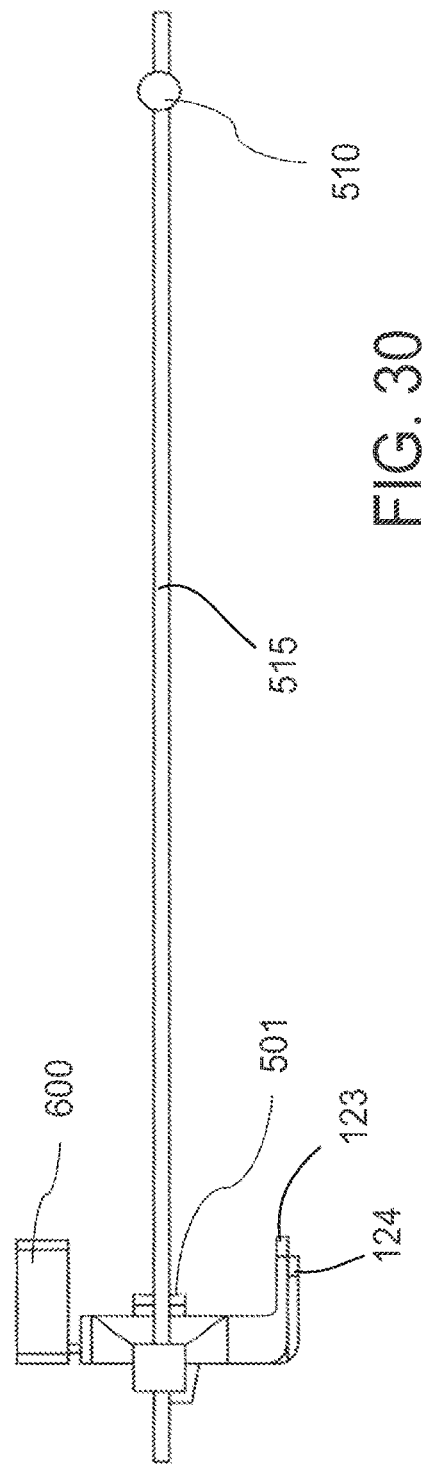
FIG. 29
FIG. 30

ALIGNMENT DEVICES AND METHODS

CROSS-REFERENCE TO RELATED APPLICATIONS

This application is a divisional application of U.S. patent application Ser. No. 14/433,866, filed on Apr. 7, 2015, and titled "Alignment Devices and Methods," which is a U.S. national stage filing under 35 U.S.C. § 371 of International PCT Application No. PCT/US13/65730 filed Oct. 18, 2013, and titled "Alignment Devices and Methods," which claims priority to and the full benefit of U.S. Provisional Patent Application No. 61/715,631, filed Oct. 18, 2012. The entirety of each is incorporated by reference herein.

BACKGROUND OF THE INVENTION

The present invention relates generally to the installation of orthopedic implants with respect to patient physiology and function, and particularly to joint alignment and balancing devices and methods for arthroplasty implants.

A common source of early wear and revision of orthopedic implants is improper alignment of the orthopedic implants relative to the natural physiology of the patient. Over the years, many sophisticated machines and instruments have been tried to improve alignment of orthopedic implants. However, many of these machines and instruments are expensive and have not been readily adopted. For example, computer assisted surgery ("CAS") provides highly accurate tracking of implant and anatomic structures and provides exceptional three-dimensional models. The CAS machines and software, as well as maintenance, can be a significant capital expenses to healthcare providers, which may or may not be reimbursed. Also, pre-operative three-dimensional models are not always particularly useful to a surgeon where the surgeon is more likely to have only x-ray (radiograph) equipment available to assist with evaluation of the surgery. MRI scans or CT scans simply often may not be available. The volume and format of information provided by some of the more sophisticated tools may, in fact, have a negative effect on surgical efficiency and efficacy. Many arthroplasty instruments have relied on penetration of the medullary canal of the bone to which implant components are to be attached to achieve alignment. However, penetration of the medullary canal can lead to some complications, and avoiding the practice may benefit some patients.

Improved devices and methods may rely on less expensive, more common, and more reliable imaging solutions such as a radiograph. Improved devices may provide the right amount of useful information when information is needed and in ways that are complementary to current surgeon preferences and practices. It may also be useful to provide surgeons with preoperative information in the same format that they can expect to receive information intraoperatively. Similarly, postoperative information provided in a like format may assist surgeons with more accurate evaluations of the operations performed. Providing information that is useful in simplifying complex decisions that are dependent on variable inputs and factors may also be beneficial. It may also be beneficial to provide patient-matched ("PM") instruments that have been generated through the use of radiographs rather than through more costly and less available imaging devices. Improved instruments may also achieve physiologically appropriate alignment without penetrating the medullary canal.

SUMMARY OF THE INVENTION

In one general aspect, an alignment guide for implanting an implant component in a patient includes a body for alignment with respect to a bone of the patient. The body includes an aperture extending at an angle relative to an axis, and an offset portion configured to intersect a plane that extends through a physiological reference on the bone when the body is aligned with respect to the axis.

An embodiment of the invention is a femoral implant alignment guide for implanting a femoral component in a patient. The femoral implant alignment guide may include a body configured to be placed on a distal end of a femur and be aligned on an axis from between the patient's femoral condyles through the patient's hip center. The body of the guide may also include an elongated resection aperture with a major axis substantially perpendicular to the axis through the patient's hip center when the body is aligned on the axis through the patient's hip center, and an offset portion containing a slot or hole that is configured to extend to a point in a coronal plane of the patient that is shared with the patient's greater trochanter. This point may be directly lateral of the patient's greater trochanter. The offset portion in some embodiments is coupled to the body such that the body and the offset portion are substantially constrained from rotational displacement in coronal and/or sagittal planes of the patient.

Another embodiment of the invention is a method of manufacturing a femoral implant alignment guide configured to be used with a particular patient. The embodiment includes evaluating one or more images of the patient's anatomy that include the patient's hip and the patient's knee and defining an axis from between the patient's femoral condyles through the patient's hip center. The method may also include forming a patient-matched body that includes an elongated resection aperture that when placed against the patient's femoral condyles includes a major axis that is substantially perpendicular to the axis from between the patient's femoral condyles through the patient's hip center.

Still another embodiment of the invention is a method of implanting an arthroplasty device that includes providing a first instrument for aligning a first component of the arthroplasty device, wherein the first instrument includes an offset portion that is configured to extend to a physiological reference point that provides an alignment reference for placement of the first component. The method may also include aligning the first instrument with two or more physiological reference points and removing tissue adjacent to the first instrument to prepare a location to receive the first component. The method may also include providing a second instrument for aligning a second component of the arthroplasty device, wherein the second instrument includes an interface configured to couple with the location prepared to receive the first component, and aligning the second instrument with the location prepared to receive the first component. The method may include positioning tissue adjacent to the second instrument such that tissue adjacent to the first instrument is positioned appropriately relative to the tissue adjacent to the second instrument, removing tissue adjacent to the second instrument to prepare a location to receive the second component, implanting the first component of the arthroplasty device, and implanting the second component of the arthroplasty device.

Another embodiment of the invention is a method of implanting a knee arthroplasty device in a patient that includes provision of a femoral implant alignment guide for implanting a femoral component of the knee arthroplasty device in a patient comprising a body configured to be placed on a distal end of a femur and defining an axis from between the patient's femoral condyles through the patient's hip center. The body may include an elongated resection aperture with a major axis that is substantially perpendicular to the axis directed through the patient's hip center when the body is aligned on the axis through the patient's hip center, and an offset portion that is configured to extend to a point in a coronal plane of the patient that is shared with the patient's greater trochanter wherein the point is directly lateral of the patient's greater trochanter and wherein the offset portion is coupled to the body such that the body and the offset portion are substantially constrained from rotational displacement in a coronal and/or sagittal plane of the patient. The method may also include aligning the femoral implant alignment guide with two or more physiological reference points and removing at least a portion of the femoral condyles along a plane defined by the elongated resection aperture. The method also includes provision of a tibial implant alignment guide for aligning a tibial component of the knee arthroplasty device, wherein the tibial implant alignment guide includes an interface configured to couple with the patient's femur. The method may also include aligning and coupling the tibial implant alignment guide with the patient's femur, positioning the patient's tibia appropriately relative to the patient's femur and coupling the tibial implant alignment guide to the patient's tibia, removing at least a portion of the patient's tibia in a configuration to receive a tibial component of the knee arthroplasty device, implanting a femoral component of the knee arthroplasty device, and implanting a tibial component of the knee arthroplasty device.

Yet another embodiment of the invention is a method of implanting a knee arthroplasty device in a patient that may include imaging at least the patient's femur and proximal tibia, defining an axis on one or more images from between the patient's femoral condyles through the patient's hip center, and sizing a femoral implant alignment guide based on images of the patient's femur such that an elongated resection aperture in the femoral implant alignment guide has a major axis substantially perpendicular to the axis between the patient's femoral condyles and the patient's hip center when the femoral implant alignment guide is placed against the patient's femoral condyles. The method may also include aligning an offset portion of the femoral implant alignment guide with a point in a coronal plane of the patient that is shared with the patient's greater trochanter, wherein the point is directly lateral of the patient's greater trochanter, and aligning the femoral implant alignment guide with one or more physiological reference points on the distal femur. The method may include removing at least a portion of the femoral condyles along a plane defined by the elongated resection aperture, coupling a tibial implant alignment guide to the patient's femur at least in part where at least a portion of the femoral condyles were removed, positioning the patient's tibia appropriately relative to the patient's femur and coupling the tibial implant alignment guide to the patient's tibia, and removing at least a portion of the patient's tibia in a configuration to receive a tibial component of the knee arthroplasty device. The method may also include implanting a femoral component of the knee arthroplasty device and a tibial component of the knee arthroplasty device.

An additional embodiment of the invention is a method of providing information useful for implanting an orthopedic implant that includes providing a patient-matched instrument that includes a sensor for measuring force applied to the patient-matched instrument, placing the patient-matched instrument between two or more of: orthopedic instruments, orthopedic implant components, and bones, and reading forces and/or locations of forces applied during the alignment of two or more orthopedic instruments, orthopedic implant components, and bones. The method may also include the re-zeroing of the force sensor output in a particular patient-specific loading condition, altering the shapes or alignment of one or more orthopedic instruments, implant components and bones or other tissue, evaluating the change in the force sensor output, accepting the measured force delta or altering one or more of the orthopedic instrument, orthopedic implant components, and bones or other tissue to alter the measured force delta.

An additional embodiment of the invention is the representation of all pre-op plan information used to design the PM instrument and predict alignment outcomes within the context of one or more pre-operative radiographs. This radiographic preoperative plan is also used as a verification tool when overlaid over or otherwise compared with the postoperative radiograph.

Further areas of applicability of the invention will become apparent from the detailed description provided hereinafter. It should be understood that the detailed description and specific examples, while indicating the particular embodiment of the invention, are intended for purposes of illustration only and are not intended to limit the scope of the invention.

BRIEF DESCRIPTION OF THE DRAWINGS

The accompanying drawings are incorporated in and form a part of the specification, illustrate the embodiments of the invention, and together with the written description serve to explain the principles, characteristics, and features of the invention. In the drawings:

FIG. 1 is an anterior to posterior radiograph of a patient's femur, hip, and knee.

FIG. 2 is an anterior to posterior radiograph of a patient's knee.

FIG. 15B is an anterior elevation view of the instrument of FIG. 15A shown having a variety of medial and lateral offset surfaces.

FIG. 15C is an anterior elevation view of a modular embodiment of the instrument of FIG. 15B.

FIG. 15D is an exploded view of the modular instrument of 15C.

FIG. 23 is a distal end view of a femoral alignment guide engaged with a femur.

FIG. 29 is a side view of the femoral alignment guide and femur of FIG. 23, with the second guide of FIGS. 26-28.

FIG. 30 is a side view of the femoral alignment guide of FIG. 23 with the second guide of FIGS. 26-28.

DETAILED DESCRIPTION OF THE EMBODIMENTS

Figure 3A:
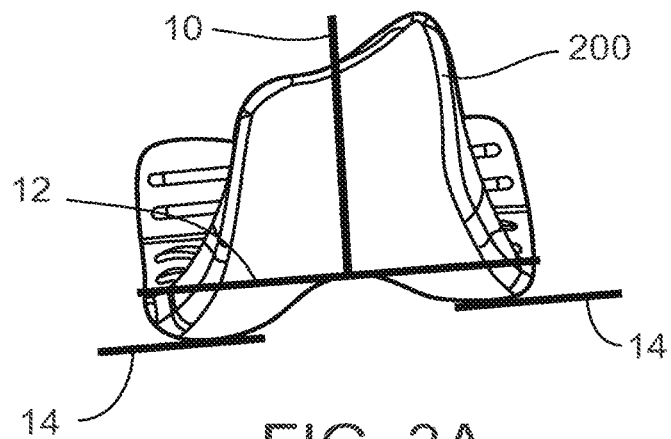
FIG. 3A is front elevation view of a femoral component of a knee arthroplasty device.
Figure 3B:
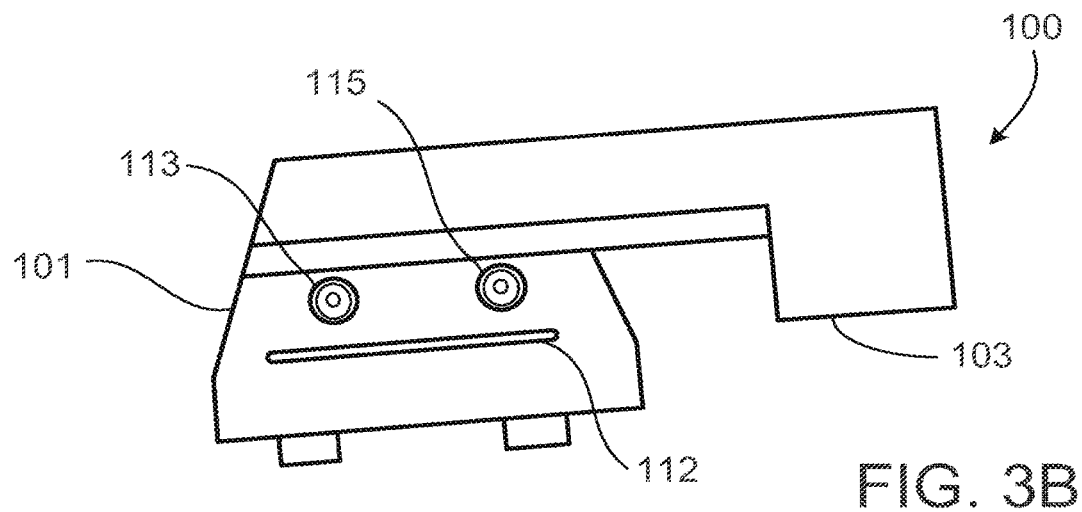
FIG. 3B is a front elevation view of a femoral implant alignment guide.

The following descriptions of the depicted embodiments are merely exemplary in nature and are in no way intended to limit the invention, its application, or uses.

An anterior to posterior radiograph of a patient's femur 1, hip 3, and knee 5 is shown in FIG. 1. FIG. 2 shows the patient's femur 1, knee 5, and tibia 2. The images provided in FIGS. 1 and 2 are radiograph images produced with x-rays. In some embodiments, other imaging techniques and devices may be used, but in this embodiment, radiograph images are used to capture preoperative information for the manufacture of an alignment guide and for comparison with postoperative alignment information. An axis 10 is illustrated in FIGS. 1 and 2 that passes between the patient's femoral condyles 4 and through the patient's hip center 11 (FIG. 1). This axis 10 is well-known to approximate an appropriate alignment for a knee arthroplasty device. An axis 12 is illustrated in FIG. 2 that is substantially perpendicular to the axis 10. This axis 12 provides a preoperative or intraoperative guide for instruments and implants that may be placed on or parallel with the axis 12. The axis 12 also provides an appropriate orientation for rotation of a knee arthroplasty device such that forces through the patient's knee may be maintained along the axis 10 without generating unwanted force eccentricities.

Figure 5:
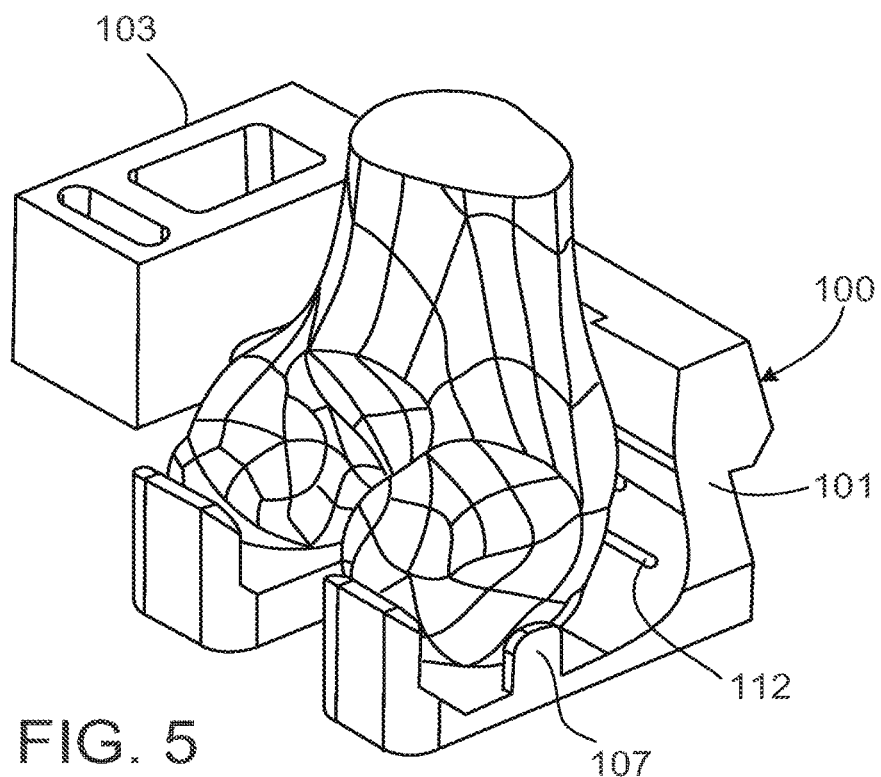
FIG. 5 is a perspective view of a distal portion of a femur in a femoral implant alignment guide.
Figure 6:
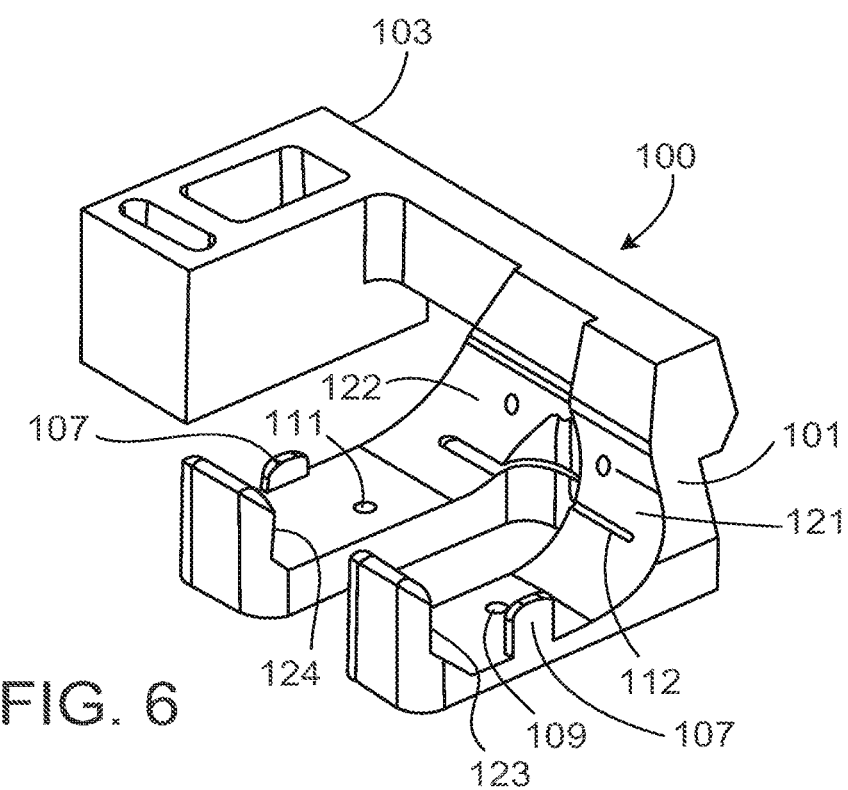
FIG. 6 is a perspective view of a femoral implant alignment guide.
Figure 7:
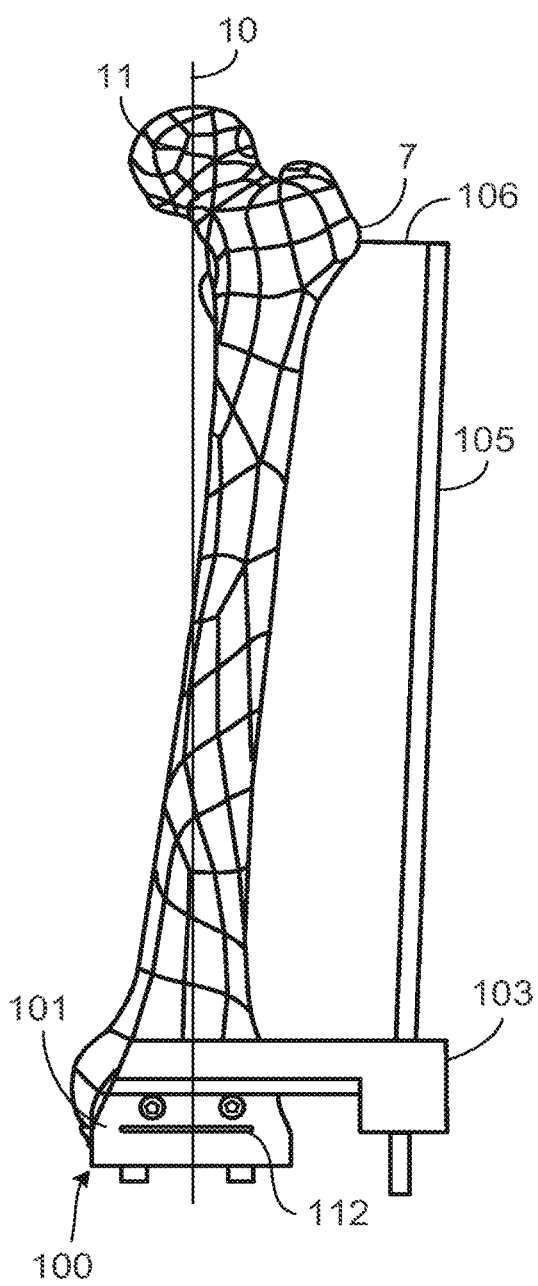
FIG. 7 is a front elevation view of a femur engaged with a femoral implant alignment guide.

A femoral implant alignment guide 100 is illustrated in FIGS. 3B, 3C and 5-10. The femoral implant alignment guide 100 in the illustrated embodiment is for implanting a femoral component of a total knee arthroplasty device in a patient. While this embodiment is directed to a knee arthroplasty device, in other embodiments instruments for aligning other types of arthroplasty and orthopedic devices are also contemplated. For example and without limitation, instruments for implanting hip, shoulder, spine, and other devices having altered attachment mechanisms and sizing but similar structure or function are contemplated. The femoral implant alignment guide 100 includes a body 101 and an offset portion 103. The body 101 is configured to be placed on a distal end of a femur 1 (FIGS. 5 and 7-10) and to be aligned on the axis 10 (FIGS. 3C and 7) from between the patient's femoral condyles 4 (FIGS. 1 and 9) through the patient's hip center 11 (FIGS. 1 and 7).

Figure 3C:
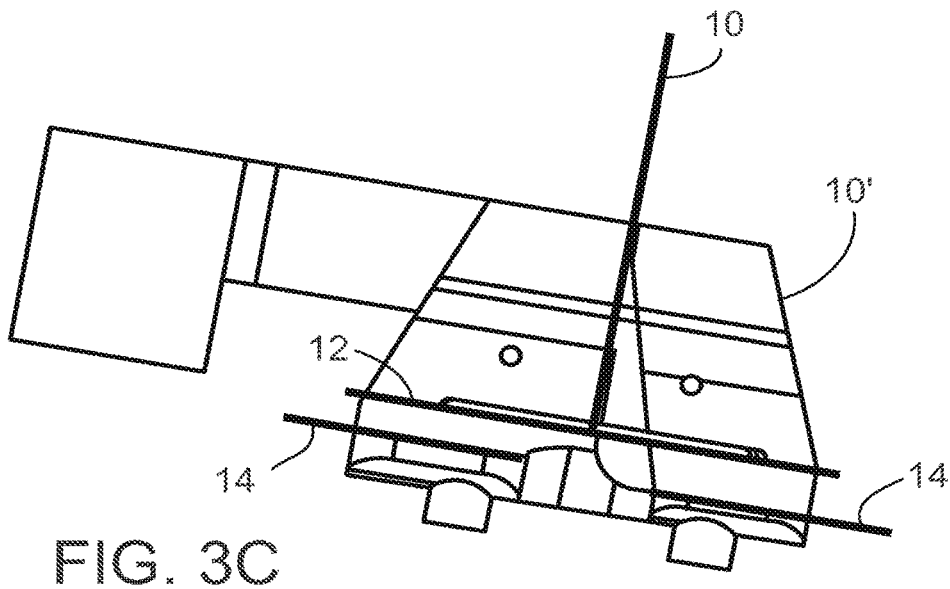
FIG. 3C is a posterior view of the femoral implant alignment guide.

The axis 12 is also illustrated in FIGS. 3A and 3C substantially perpendicular to the axis 10 and providing an alignment reference for a femoral component 200 of a knee arthroplasty device. An elongated resection aperture 112 is illustrated in FIGS. 3B, 3C, 5-7, and 9. The elongated resection aperture 112 is illustrated in FIGS. 3C and 7 with a major axis substantially perpendicular to the axis 10 through the patient's hip center 11 (FIG. 7). As illustrated, the body 100 is aligned on the axis 10 through the patient's hip center 11. This configuration may be represented in another way by stating that the elongate resection aperture 112 has a major axis substantially perpendicular to a minor axis of the body 100, or may be defined with reference to any edge or surface of the body 100. As illustrated in FIGS. 2, 3A, and 3C, the relationship between alignment and the distal femur condylar contact surfaces 14 is the same for the radiograph, implant and guide.

The hip center is commonly used to define the proximal of two points (proximal and distal) required to define the mechanical axis of the femur, though other landmarks could be used. The distal mechanical point lies between the femoral condyles in the coronal plane and can be defined using any of several landmarks visible in a substantially anterior-posterior radiograph, for example: the most distal apex of the trochlear groove or the medial-lateral center of the distal femur. The distal mechanical point lies along the femoral distal trochlear groove in the sagittal plane and can be defined using a substantially distal point along the distal trochlear groove which is visible in a substantially medial-lateral radiograph.

Figure 4:
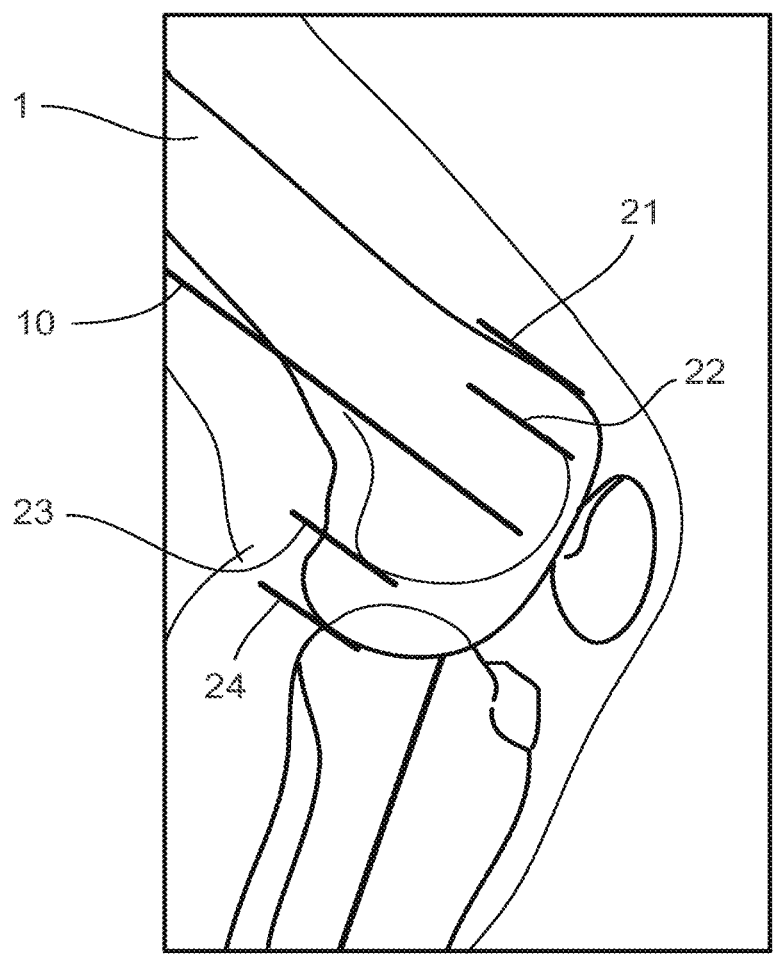
FIG. 4 is a sagittal plane radiograph of a patient's knee.
Figure 9:
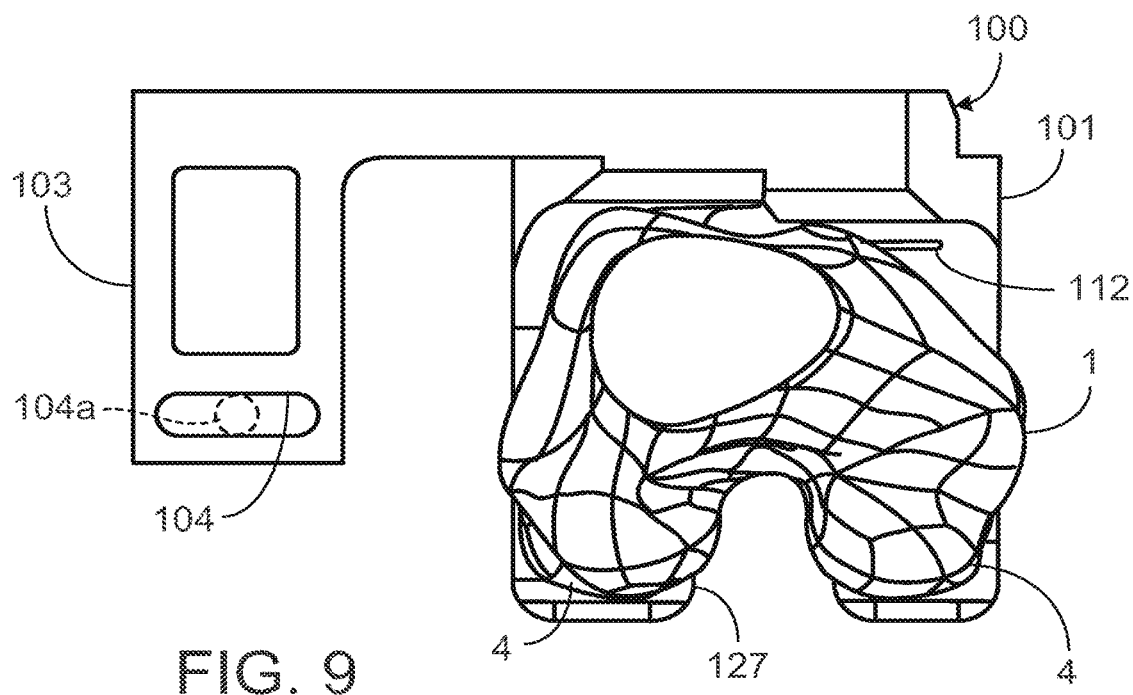
FIG. 9 is a top plan view of a distal portion of a femur in a femoral implant alignment guide.
Figure 10:
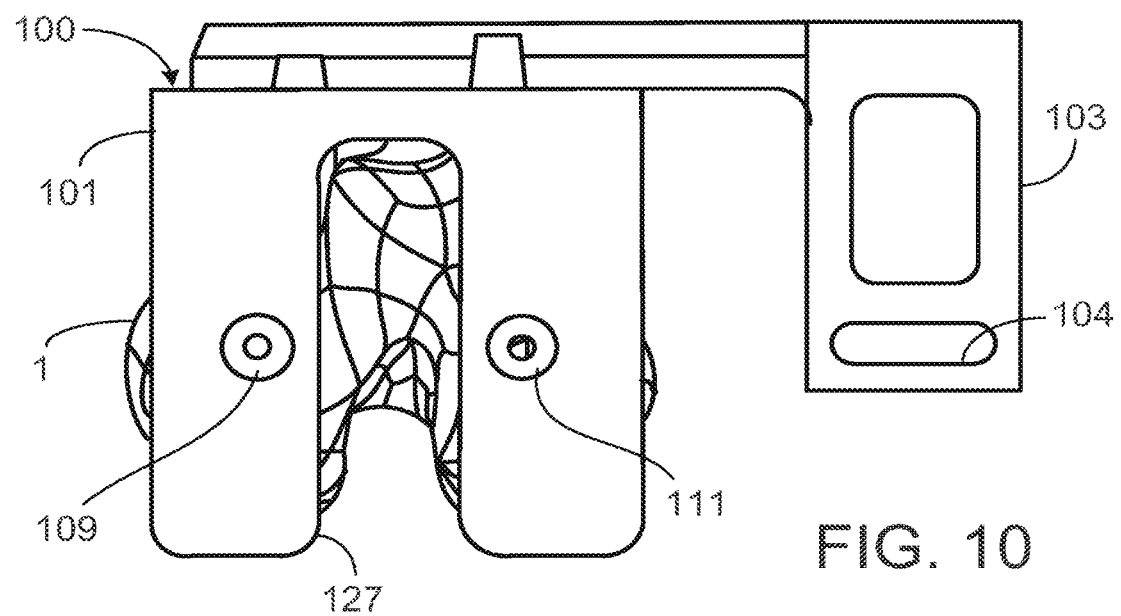
FIG. 10 is a bottom plan view of a distal portion of a femur in a femoral implant alignment guide.

A medial to lateral radiograph of a patient's knee is illustrated in FIG. 4 and includes markers 21, 22, 23, 24. An anterior to posterior radiograph of a patient's knee is illustrated in FIG. 2 and includes markers 14. The markers 14, 21, 22, 23, 24 indicate the locations of physiological reference points on the distal end of the femur 1. Markers 14 are medial and lateral distal femur condyle points. Marker 21 is a reference point for a medial anterior ridge. Marker 22 is a reference point for a lateral anterior ridge. Marker 23 is a reference point for a medial posterior condyle. Marker 24 is a reference point for a lateral posterior condyle. In some embodiments, reference points such as these may be used to generate a patient-matched instrument or be correlated with an appropriate size and fit from a set of instruments to assist with alignment of the instrument, and consequently, alignment of an implant. The markers 14, 21, 22, 23, 24 in the illustrated embodiment, are correlated with instrument size and shape references 14, 121, 122, 123, 124 in FIG. 6 and apertures 109, 111 in FIGS. 6 and 10. In some cases, these markers could be correlated to functional aspects of the knee joint, such as the Q-angle by calculating the amount of femur rotation which occurs between at least two radiographs where at least one radiograph is taken in flexion and at least one radiograph in extension. In the example shown in FIGS. 5-6, the femoral implant alignment guide 100 is a patient-matched body that includes an elongated resection aperture 112 that when placed against the patient's femoral condyles includes a major axis that is substantially perpendicular to the axis 10 (FIG. 5) from between the patient's femoral condyles through the patient's hip center. Another type of reference point alignment is illustrated in FIGS. 9-10. As shown in this embodiment, the femur 1 may be visually aligned through the window 127 relative to the femoral implant alignment guide 100. This gives a surgeon options with regard to aligning as preoperative planned or making modifications intraoperatively. It is contemplated that the femoral implant alignment guide may be aligned with these or any other effective physiological reference points on the femur 1.

Figure 8:
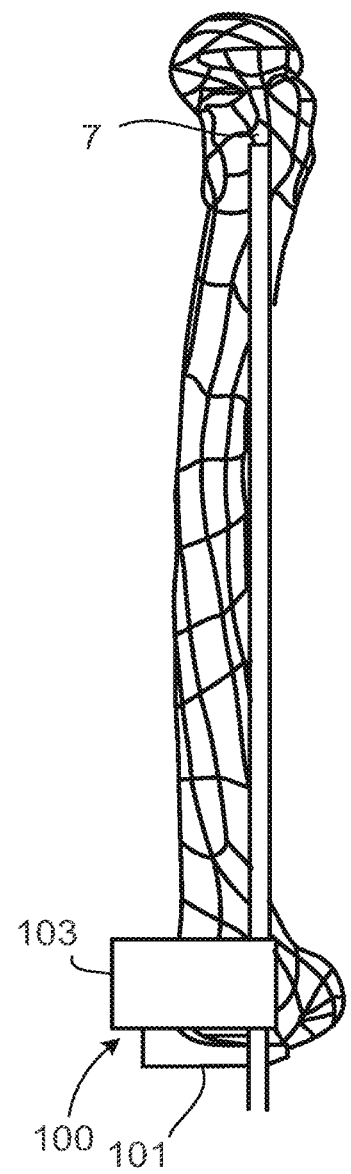
FIG. 8 is side elevation view of a femur engaged with a femoral implant alignment guide.

The offset portion 103 in the illustrated embodiment is configured to extend to a point in a coronal plane of the patient that is shared with the patient's greater trochanter. As illustrated in FIGS. 7-8, this point is directly lateral of the patient's greater trochanter 7. The offset portion 103 shown, in addition to the portion coupled to the body 101, includes a slot 104 (FIGS. 9-10) and a rod 105 (FIG. 7). The rod 105 is configured to engage in the slot 104. In most cases, the greater trochanter 7 can be assumed to adequately approximate a patient's hip center in a sagittal view, or an offset can be measured radiographically. Thus, the greater trochanter 7 can be used as a preoperatively visible and intraoperatively accessible surrogate for the hip center for the purpose of sagittal alignment. Because the rod 105 is able to pivot or translate in the slot 104, the variations in soft tissue thickness between the greater trochanter 7 and the skin can be accounted for intraoperatively without affecting the sagittal position of the rod 105 or the coronal alignment of the guide.

In the sagittal plane, the relationship between the alignment guide 100 and distal mechanical point in the sagittal plan is preoperatively designed and intraoperatively constrained by references 121, 122, 123, 124. The relationship between the alignment guide 100 and the proximal mechanical point in the coronal plane is preoperatively designed and intraoperatively constrained by the rod 105, length of the needle 106 from tip to rod interface, and distance between the most lateral point of the greater trochanter and the proximal mechanical point, commonly defined by the hip center. The relationship between the alignment guide 100 and the proximal mechanical point in the sagittal plane is preoperatively designed and intraoperatively constrained by the substantial perpendicularity of the rod 105 to the elongated resection aperture 112, the substantially medial-lateral orientation of the needle 106, and the distance between the most lateral point of the greater trochanter and the proximal mechanical point in the sagittal plane which can be measured in a substantially medial-lateral radiograph or correlated to the patient type (height, sex, ethnicity, etc.) or assumed to be a constant across all patients. The sum of the designed and constrained relationships in the sagittal plane allows the intraoperatively constrained alignment between the elongated resection aperture 112 and mechanical axis of the femur (FIG. 22) to be substantially similar to the preoperatively planned alignment. Thus, the greater trochanter 7 can be used as a preoperatively visible and intraoperatively accessible surrogate for the proximal mechanical point for the purpose of sagittal alignment.

The offset portion 103 can include a cylindrical bore (shown in dashed line in FIG. 9) rather than a slot 104, such that the rod 105 is additionally constrained in the coronal plane. In the coronal view, an offset between the hip center and the most lateral point of the greater trochanter is measurable using an anterior-posterior radiograph (FIG. 7). Also in the coronal view, an offset between the most lateral point of the greater trochanter 7 and the skin is measurable using an anterior-posterior radiograph. Both measured offsets can factor into coronal alignment of an alignment guide 100, rod 105 and needle 106. The aforementioned trochanter to skin offset is intraoperatively bridged by insertion of the needle 106 through the skin until the tip contacts the later point of the greater trochanter. The needle 106 is joined proximally to the rod proximally near the location of the greater trochanter and has a controlled length from tip to rod interface which is designed to ensure that the tip of the needle can reach the greater trochanter while maintaining its connection to the rod. At least the following medial-lateral distances are used to ensure the design of the alignment guide 100, rod 105 and needle 106 result in the alignment of the elongated resection aperture to the femur mechanical axis in the coronal plane: the designed distance between the distal mechanical point and the alignment guide 100/distal rod 105 interface, the designed distance between the proximal rod 105/lateral needle 106 interface and the medial needle tip, and the measured distance between the most lateral point of the greater trochanter and the proximal mechanical point. The relationship between the alignment guide 100 and the distal mechanical point in the coronal plane is preoperatively designed to be intraoperatively constrained by tabs 107. The sum of the designed and constrained relationships in the coronal and sagittal planes allows the intraoperatively constrained relationship between the elongated resection aperture 112 and mechanical axis of the femur (FIG. 22) to be substantially similar to the preoperatively planned relationship. Thus, the greater trochanter 7 can be used as a preoperatively visible and intraoperatively accessible surrogate for the hip center for the purpose of sagittal and coronal alignment.

In order to facilitate the surgeon's fine-tuned placement of the needle tip, the rod may be preoperatively designed to a length consistent with the distance between distal and proximal mechanical points of the femur. In order to limit error in the position of the needle tip, the rotation of the rod about its axis is constrained such that the needle points in a substantially medial-lateral direction.

The femoral implant alignment guide 100 can include tabs 107 (FIGS. 5 and 6) for constraining medial/lateral position of the guide 100 to a preoperatively defined position relative to the distal femur 1. The tabs 107 are spaced based on x-ray measures and can be made flexible to accommodate a tighter fit or possible error in the x-ray measurement.

The relationships between coronal alignment of some apertures 112, 1001, 1002 and distal femur condylar contact surfaces 14 are isomorphic with the relationships between the femur coronal alignment and the most distal femur medial and lateral condylar points 14. The relationships between the rotational alignment of some apertures 109, 111 and the medial and lateral anterior femoral ridges contact surfaces 121, 122 are isomorphic with the relationship between the leading medial and lateral anterior femoral ridges 21, 22 and the Q-angle as calculated by the inferred rotation of the femur occurring between extension and flexion as measured by at least two lateral x-rays. The relationships between the rotational alignment of some apertures 109, 111 and the medial and lateral posterior femoral condylar contact surfaces 123, 124 are isomorphic with the relationship between the medial and lateral posterior femoral condylar tangencies 23, 24. The relationship between the medial-lateral position of some apertures 112, 1001, 1002, 109, 111 and the medial and/or lateral constraining surfaces 107 is isomorphic with the medial to lateral width of the distal femur 1003.

Figure 11:
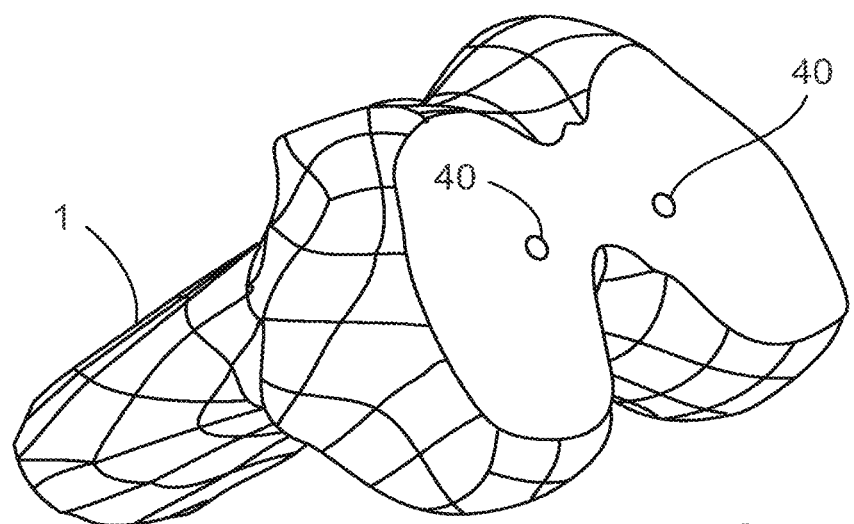
FIG. 11 is a perspective view of a partially resected distal portion of a femur.
Figure 12:
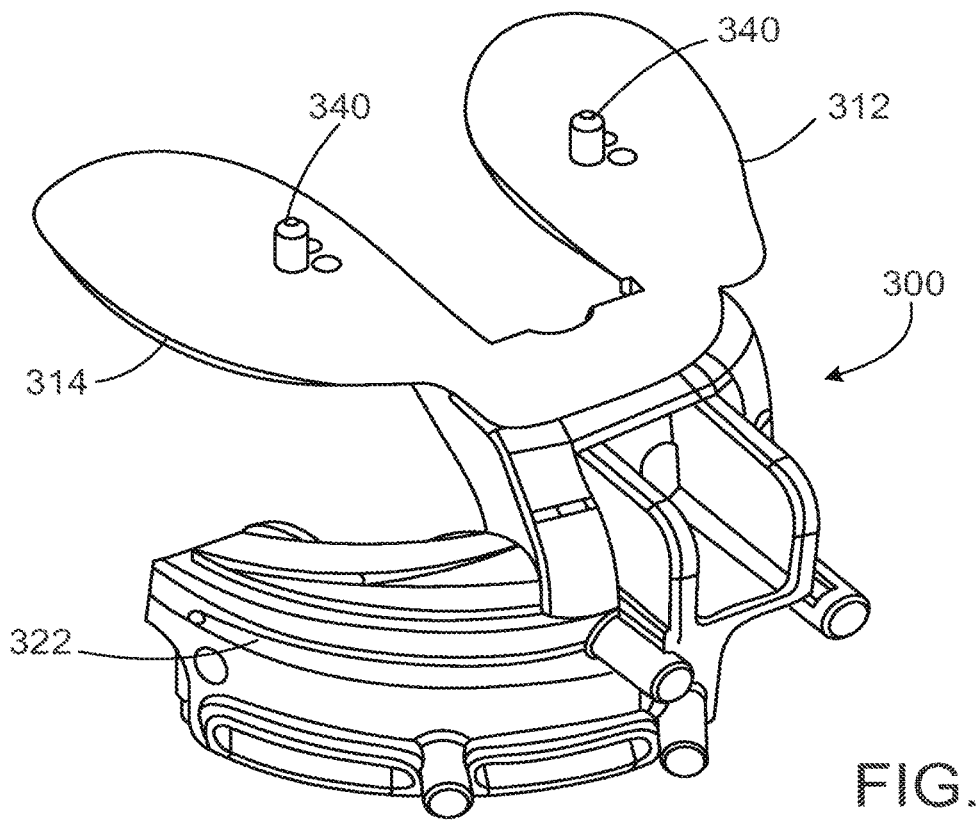
FIG. 12 is a perspective view of a tibial implant alignment guide.

A partially resected distal portion of a femur 1 is shown in FIG. 11. Connection holes 40 have been prepared through the resected distal portion of the femur 1. A tibial implant alignment guide 300 is illustrated in FIG. 12. Interface pins 340 that are configured to couple with connection holes 40 are also depicted. The tibial implant alignment guide 300 is a known device that is disclosed in detail in U.S. Prov. Pat. Appl. Ser. Nos. 61/681,475 and 61/715,462, both entitled PATIENT-MATCHED TOTAL KNEE ARTHROPLASTY, and filed on Aug. 21, 2012 and Oct. 18, 2012 respectively, each of which is hereby incorporated by reference in its entirety.

Figure 16A:
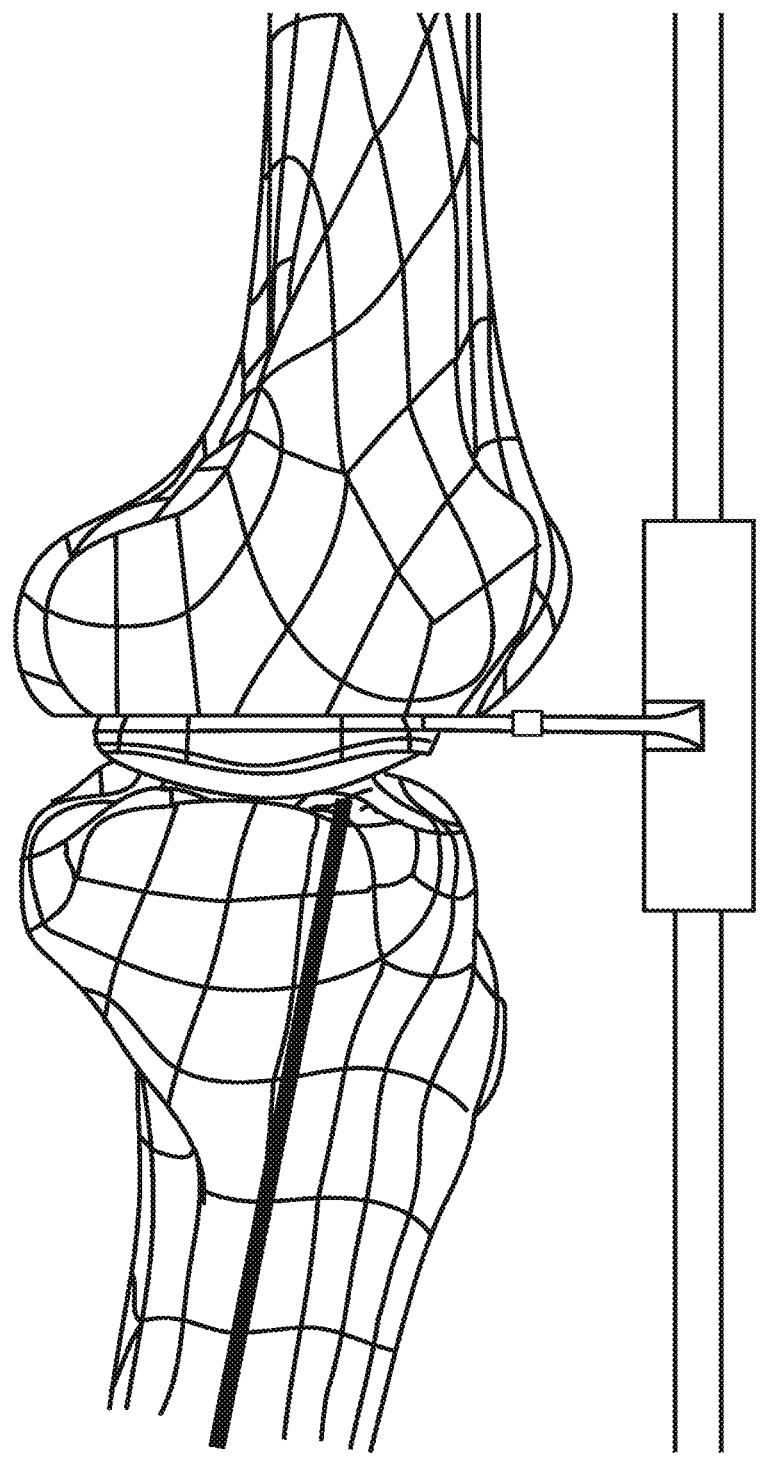
FIG. 16A is a side elevation view of an alternative embodiment of the instrument of FIG. 15 between a tibia and femur where the tibia is unable to achieve full terminal extension.

In general, the tibial implant alignment guide 300 includes a distal femur gauge including medial and lateral condyle paddles 312, 314 each having a shape and size corresponding to a pre-operative planned distal resection of a patient's femur. In this case, the resections correspond to the tissue removed from the femur illustrated in FIG. 11. The tibial implant alignment guide 300 shown also includes a cutting block component with an elongated resection aperture 322. When the tibial implant alignment guide 300 is coupled with the femur 1 and the positions of the patient's tibia and femur are brought into appropriate relative positions, a portion of the patient's tibia can be resected so that a tibial component of a knee arthroplasty device can be accurately placed. More particularly regarding determining appropriate fit when the tibia and femur are in appropriate relative positions, a surgeon may put the leg in extension and place the distal-facing surfaces of the condyle paddles 312, 314 against the native tibia, as similarly illustrated in FIG. 16B. If the limb cannot return to full extension (i.e. flexion contracture FIG. 16A), then this indicates that too little distal femur has been resected. By how much the distal femur has been under resected can be gauged by simulating a distal femur recut through removing thickness from the distal femur gauge in increments of 1 mm, as described in US Published Application No. 2010/0305575, titled Method and Apparatus for Performing Knee Arthroplasty, hereby incorporated by reference in its entirety. It has been found that 1 mm of distal femur gauge thickness reduction will allow between 1 and 2 degrees of additional extension. If instead of flexion contracture, the limb exhibits hyperextension, this indicates that too much distal femur has been resected. Material can then be added to the thickness of the condyle paddles in 1 mm increments resulting in 1-2 degrees of reduced extension. In this way one can gauge exactly how much the distal femur has been under or over resected relative to the native joint line as represented by the native tibial articular geometry. This information is useful as it can directly or indirectly affect subsequent decisions and outcomes.

Figure 13A:
FIG. 13A is a view of the representations of portions of a femur that have been resected derived from a sagittal radiograph of the femur prior to resection.
Figure 13B:
FIG. 13B is a view of the representations of portions of a femur that have been resected derived from a coronal radiograph of the femur prior to resection.
Figure 14A:
FIGS. 14A and 14B are perspective views of representations of portions of a femur that have been resected derived from sagittal and coronal views of the femur prior to resection.
Figure 14C:
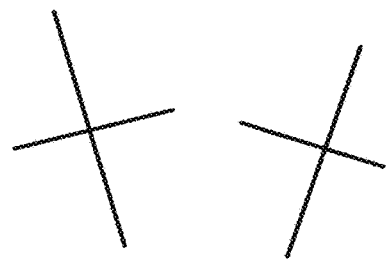
FIGS. 14C and 14D are plan views of representations of portions of a femur that have been resected showing orientations and sizes of the resected portions of the femur prior to resection.
Figure 14B:
Figure 14D:
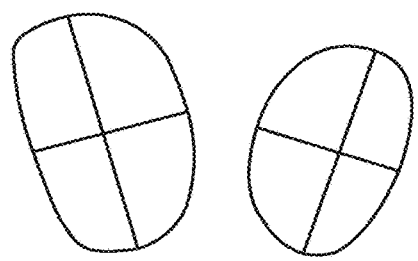
Figure 15A:
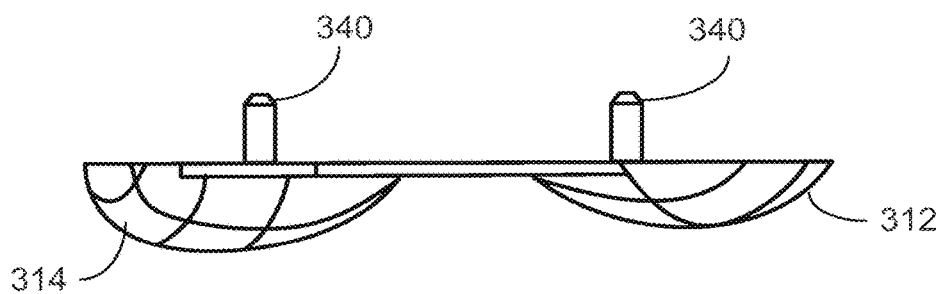
FIG. 15A is an anterior elevation view of an instrument derived from the size and shape of the resected portions of the femur illustrated in FIGS. 13B and 14B.

FIGS. 14A and 14B illustrate representations of portions of a femur that have been resected. The illustrated shapes were derived from sagittal (FIG. 13A) and coronal (FIG. 13B) views of the femur prior to resection, and consequently, are consistent with information that can be obtained from standard radiographic images. CAD software has been used to assist with defining the volumetric shapes illustrated in FIG. 14B. FIGS. 14C and 14D show representations of portions of a femur that have been resected showing orientations and sizes of the resected portions of the femur prior to resection. CAD software has been used to assist with defining the likely curvatures, as shown in FIG. 14D. The orientation of these likely curvatures are needed for understanding how to best match the anatomy; however, are not visible in radiographs. Though early data shows that the orientation could mismatch as much as 10 degrees with negligible effect on alignment, alternative sources of data (patient height, sex, ethnicity, etc.) could be used to infer, calculate and predict the orientation of these likely curvatures in order to minimize mismatch. These shapes are used to derive a distal femur gauge portion of a tibial implant alignment guide 300 including medial and lateral condyle paddles 312, 314, as illustrated in FIGS. 12 and 15A. Inclusion of the standing coronal deformity and maximum passive extension of the limb could be included to further educate the design of the instrument.

A method embodiment of the invention is a method of manufacturing a femoral implant alignment guide, such as but not limited to, the femoral implant alignment guide 100 configured to be used with a particular patient. Embodiments of this method include evaluating one or more images of the patient's anatomy that include the patient's hip and the patient's knee. For example, evaluating FIGS. 1 and 2. The method may also include defining an axis from between the patient's femoral condyles through the patient's hip center. This definition is illustrated by the axis 10 that passes through the patient's hip center 11 and between the patient's condyles 4. Another act of the embodiment is forming a patient-matched body that includes an elongated resection aperture that when placed against the patient's femoral condyles includes a major axis that is substantially perpendicular to the axis from between the patient's femoral condyles through the patient's hip center. The femoral implant alignment guide 100 demonstrates such a patient-matched body. The markers 21, 22, 23, 24 in the illustrated embodiment, are correlated with instrument size and shape references 121, 122, 123, 124 in FIG. 6. In the example shown in FIGS. 5-6, the femoral implant alignment guide 100 is a patient-matched body that includes an elongated resection aperture 112 that when placed against the patient's femoral condyles includes a major axis that is substantially perpendicular to the axis 10 (FIG. 4) from between the patient's femoral condyles through the patient's hip center.

An embodiment of the invention is a method of implanting a knee arthroplasty device in a patient. The method described herein is a total knee arthroplasty. However, in other variations the method described is applicable to partial knee replacements such as a unilateral knee replacement, and may also be applicable to other arthroplasty procedures. The femoral implant alignment guide 100 for implanting the femoral component 200, each as has been more specifically described herein, is provided as part of the method described. In the illustrated embodiment, the femoral implant alignment guide 100 is aligned with two or more physiological reference points. For example as shown in FIG. 7-8, the rod 105 is aligned with the greater trochanter 7 as a surrogate for the hip center 11. This alignment controls the tilt of the femoral implant alignment guide 100 along the sagittal plane. Similarly, alignment of the distal femur relative to the femoral implant alignment guide 100 may be accomplished, as shown in FIGS. 9-10. Particularly, the femur 1 may be visually aligned through the window 127 relative to the femoral implant alignment guide 100. This gives a surgeon options with regard to aligning as preoperative planned or making modifications intraoperatively. It is contemplated that the femoral implant alignment guide may be aligned with these or any other effective physiological reference points on the femur 1.

With the femoral implant alignment guide 100 in an appropriate location relative to the femur 1, a saw or other cutting device may be used to remove at least a portion of the femoral condyles along the plane defined by the elongated resection aperture 112, which is illustrated in FIGS. 3B, 5-7, and 9. Depending upon the configuration of the femoral component, other cuts to the femur may be necessary prior to implantation of the femoral component. Also, in some embodiments, an extension measurement may result in recognition of the need for an additional femoral cut. If this happens, an additional cut through the femoral implant alignment guide 100 or a cut separate from the femoral implant alignment guide 100 may be necessary to ensure proper fit of the arthroplasty device.

In an additional act of the method, the tibial implant alignment guide 300, as illustrated in FIG. 12, is provided to assist with aligning the tibial component of the knee arthroplasty device by making an appropriate cut on the tibia 2. The tibial implant alignment guide 300 includes a distal femur gauge including medial and lateral condyle paddles 312, 314. These condyle paddles 312, 314 along with the interface pins 340, which are configured to couple with connection holes 40 in the femur 1, provide an interface with the patient's femur, such as the femur 1 illustrated in FIG. 11. Other devices and techniques for aligning and coupling the tibial implant alignment guide 300 with the patient's femur 1 may be effective as well. For example, an alternative embodiment for a tibial alignment guide is illustrated in use in FIG. 16B. This alternative embodiment alignment guide does not include an integrated component that provides a guide for resection of the tibia 2. However, it is useful in achieving alignment of the tibia 2 and the femur 1.

In a further act of this method embodiment, the patient's tibia 2 is appropriately positioned relative to the patient's femur 1. An appropriate positioning provides for recovered or corrected anatomical alignment of the patient. An additional consideration is the balancing of soft tissues adjacent to the knee such that the joint operates with even pressures and wear to the implant components. For the tibial implant alignment guide 300 illustrated in FIG. 12, the condyle paddles 312, 314 and their connecting components may be separated from the lower portion of the instrument such that after an alignment is accomplished with the patient's leg extended, the patient's leg may be flexed prior to cutting of the tibia 2. When aligning and positioning is complete and the tibial implant alignment guide 300 has been coupled to the tibia 2, a portion of the patient's tibia can be removed with a saw or other cutting device such that the tibia 2 is configured to receive a tibial component of the knee arthroplasty device. To complete some embodiments of the invention a femoral component, such as the femoral component 200 of the knee arthroplasty device, is implanted, and a tibial component is implanted.

Another embodiment of the invention is a method of implanting a knee arthroplasty device in a patient that contemplates acts that enable a successful knee arthroplasty surgery using only two-dimensional imaging techniques. Specifically, in this method images of at least a patient's femur and proximal tibia are taken, as illustrated, for example, in FIGS. 1 and 2. An additional act is to define an axis on one or more of the images from between a patient's femoral condyles through the patient's hip center, as demonstrated by the axis 10 in FIGS. 1, 2, 3A, and 3C.

As described in association with FIGS. 4-6 herein, another act of the present method is sizing the femoral implant alignment guide 100 based on images of the patient's femur 1 such that the elongated resection aperture 112 in the femoral implant alignment guide 100 has a major axis substantially perpendicular to the axis 10 when the femoral implant alignment guide 100 is placed against the patient's femoral condyles. Another act of the embodiment is to align the femoral implant alignment guide 100 with a point in a coronal plane of the patient that is shared with the patient's greater trochanter 7 (FIG. 7-8), the point being directly lateral of the patient's greater trochanter 7. Similarly, alignment of the distal femur relative to the femoral implant alignment guide 100 as shown in FIGS. 9-10 may be accomplished. Particularly, the femur 1 may be visually aligned through the window 127 relative to the femoral implant alignment guide 100. This gives a surgeon options with regard to aligning as preoperative planned or making modifications intraoperatively. It is contemplated that the femoral implant alignment guide may be aligned with these or any other effective physiological reference points on the femur 1.

FIGS. 23-29 illustrate another embodiment of the femur alignment guide designed preoperatively using at least radiographic information and which may incorporate some or all of the features of previously described embodiments. These features and some additional features described below facilitate a method of using the guide 500 to align an elongated resection aperture 112 in superior-inferior translation, sagittal and coronal alignment as well as the anterior-posterior position and internal-external rotation of a pair of cylindrical apertures 109, 111 intended to guide the making of holes 40 which together serve to provide bone modifications which constrain the alignment of subsequent instruments, resections and ultimately the femoral implant.

Figure 24:
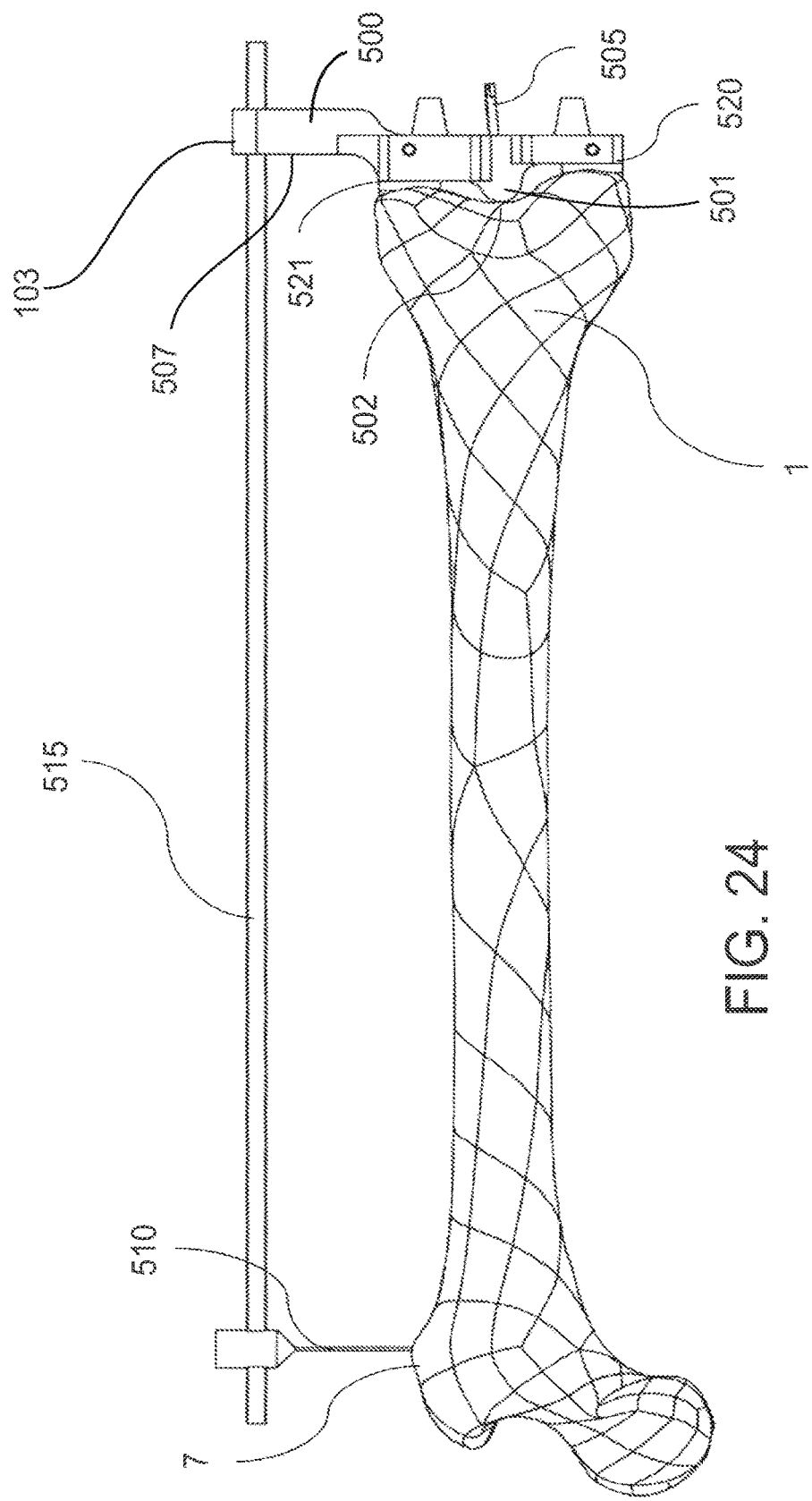
FIG. 24 is a side view of the femoral alignment guide and femur of FIG. 23.
Figure 25:
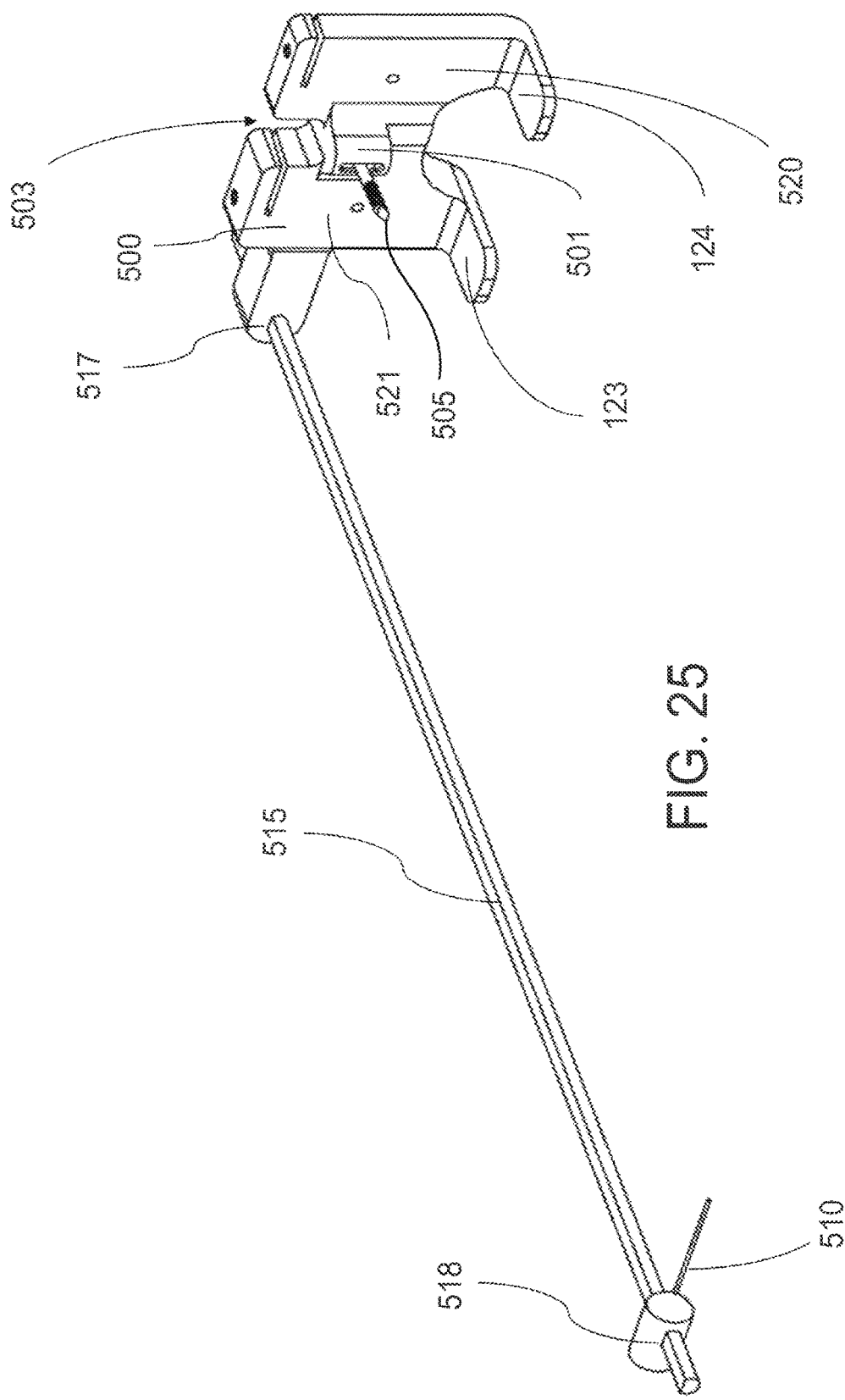
FIG. 25 is a perspective view of the femoral alignment guide of FIG. 23.

First, the guide 500 is approximately placed on the distal femur such that the trochlear probe 501 points to the distal trochlear sulcus 502 (FIG. 24). The guide 500 is then provisionally secured with a pin 505 through an elongated tapered aperture 506 which serves to grossly constrain the guide 500 to the distal femur in preparation for subsequent alignment fine tuning (FIG. 23). The shape of the elongated tapered aperture 506 is such that it allows up to at least 15 degrees of coronal, sagittal, transverse rotations and 10 millimeters of anterior-posterior translation freedom for fine-tuning.

Second, the proximal trochanter probe 510 is inserted into the skin lateral to the most lateral point of the greater trochanter 7 until the tip of the trochanter probe 510 contacts the most lateral point of the greater trochanter 7.

Figure 28:
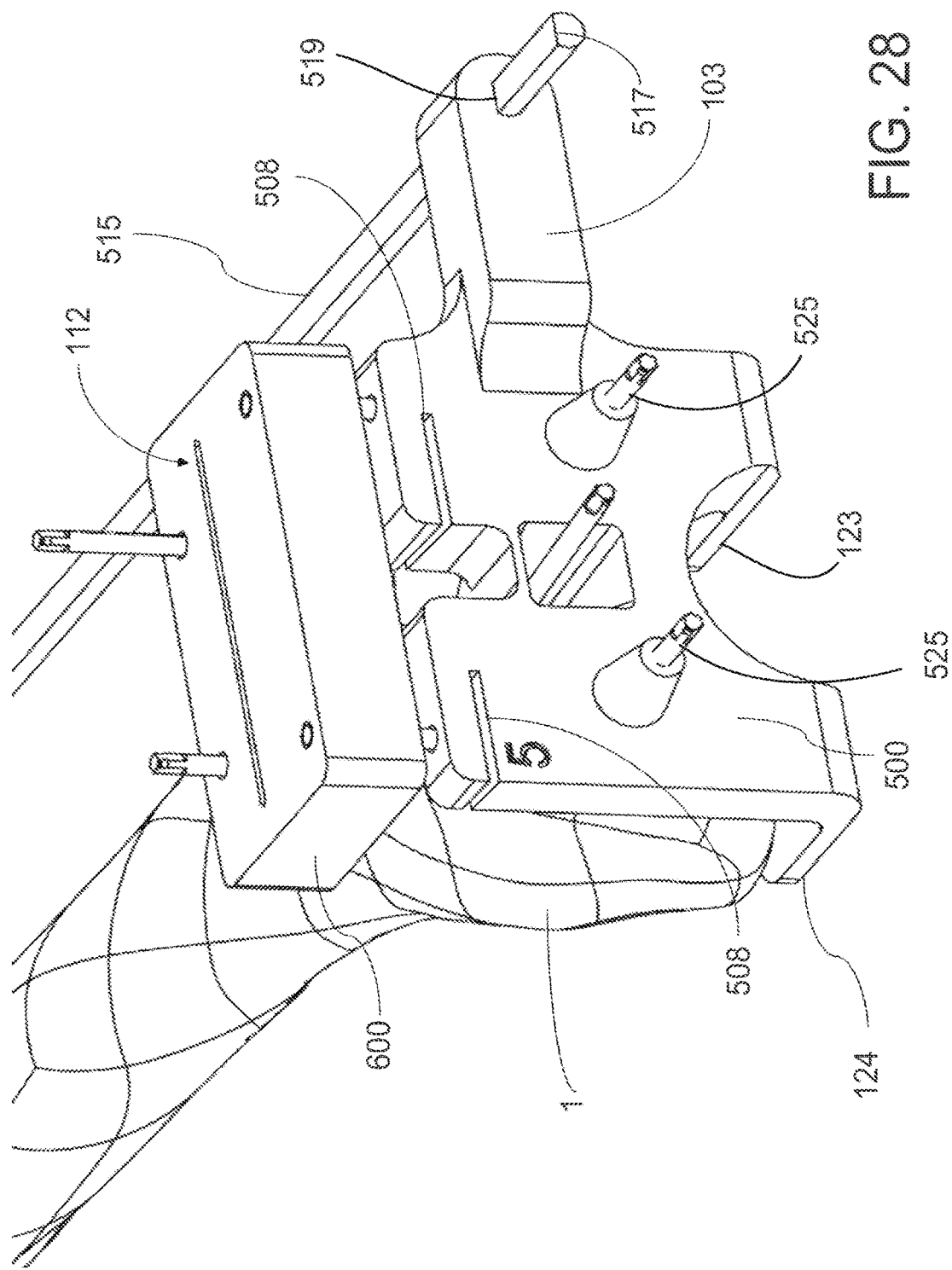

Third, the rod 515 is connected to both the trochanter probe 510 and the offset portion 103 of the guide 500 through apertures 517, 518 which constrain the rotation of the rod 515 about its long axis. One example of how rotation might be controlled is shown in FIG. 28. The rod 500 might be shaped with an orientation feature 516 such as a flat region which corresponds to apertures 517, 518 of the trochanter probe 510 and guide 500 which have a complementary orientation feature 519 clocked to a particular orientation.

With the system of guide 500, rod 515 and trochanter probe 510 mated together, and with the trochlear probe 501 pointing to the distal trochlear sulcus 502 and the trochanter probe 510 in contact with the most lateral point of the greater trochanter 7, the alignment of the guide 500 to the distal femur 1 can be fine-tuned in anterior-posterior position and internal-external rotation (FIG. 24). The guide 500 may be preoperatively configured or intraoperatively reconfigured to enable intraoperative internal-external rotation fine-tuning by removal of either the medial or the lateral posterior condyle contacts 123, 124 (FIG. 25) by frangible or modular disconnection means for example. Removal of one or the other frees the guide 500 to rotate about the desired posterior condyle in order to align the central window 503 of the guide 500 with the anterior-posterior axis 504 of the distal femur 1. Alternatively, the window 503 could be used to verify acceptable alignment with the anterior-posterior axis when both posterior condyle contacts 123, 124 are functional. If both posterior condyle contacts 123, 124 are removed, the surgeon may be able to freely adjust the anterior-posterior position of the guide while maintain desired rotational alignment between the window 503 and the anterior-posterior axis 504.

One reason a surgeon may desire to alter the anterior-posterior position of the guide 500 would be in response to the visualization of the anterior resection through slots 508, which are configured to represent the anterior resection slot. If after visualizing the anterior resection by placing a sawblade simulator in slots 508 and comparing to the anterior geometry of the distal femur 1 the surgeon predicts notching, the surgeon may opt to shift the guide 500 anterior by 1 to 4 millimeters. Indices 509 placed along the elongated tapered aperture 506 may help with measuring and controlling the amount of anterior-posterior adjustment is made (FIG. 23). Contact with the patella could impede correct alignment of the guide 500. An inferior offset 507 applied to the offset portion 103 relative to the body of the guide 500 avoids contact with the patella and associated soft tissue structures when the patella relocated laterally during surgery.

While the relationships of the probes 501, 510 to anatomic landmarks 502, 7 are maintained, coronal and sagittal alignment will simultaneously update in response to fine-tuned translation and rotation adjustments. The resection depth reference can be pre-operatively selected. In FIG. 24, the guide 500 has been preoperatively configured to reference the distal trochlear sulcus 502 for setting resection depth, as indicated by the contact made between the trochlear probe 501 and distal trochlear sulcus 502. In another embodiment the distal medial or lateral condyle might be selected as the resection depth reference. In such case, the medial or lateral condyle would be in contact with the medial contact surface 520 or lateral contact surface 521 of the guide 500.

Figure 26:
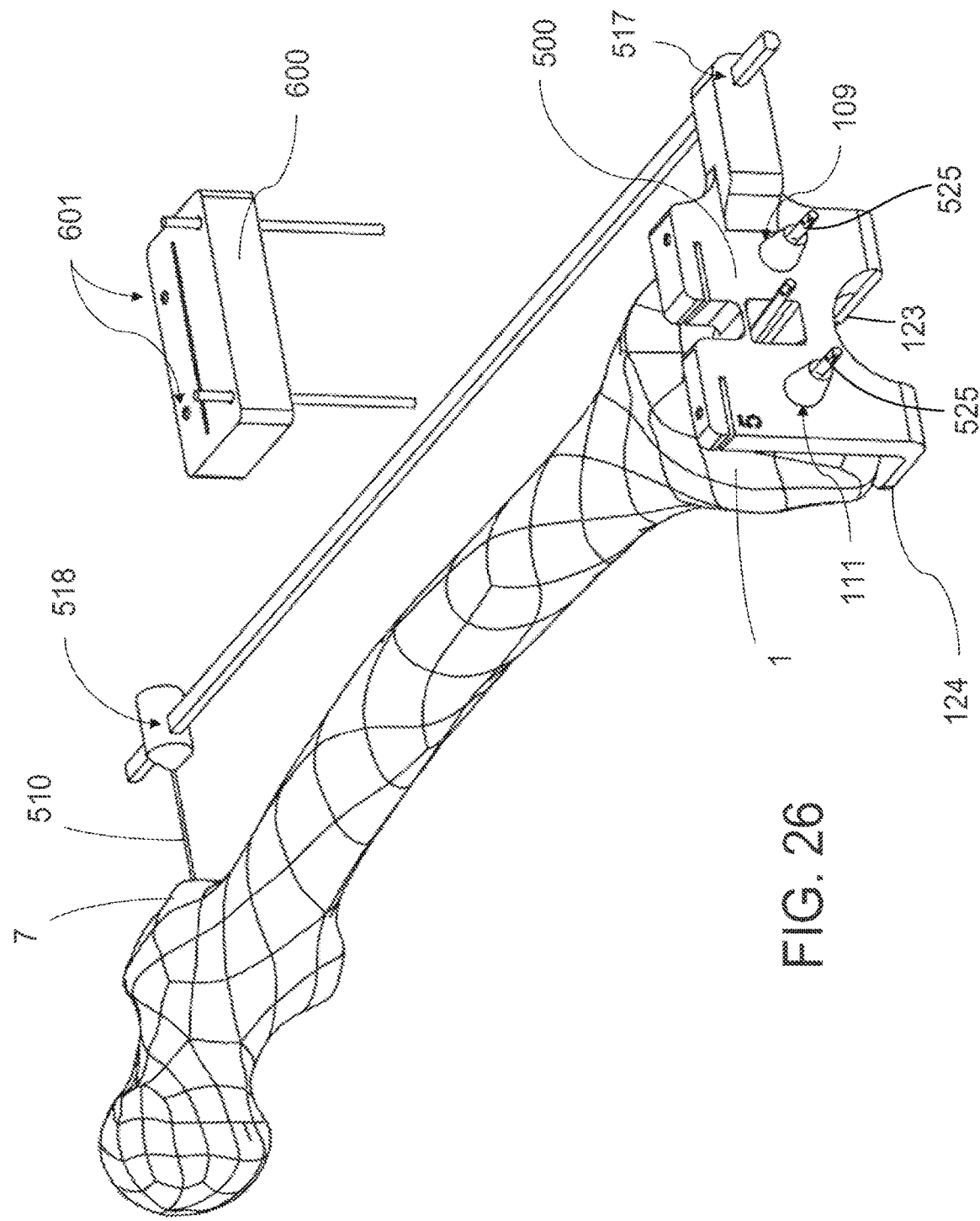
FIGS. 26-28 are perspective views of the femoral alignment guide and femur of FIG. 23 with a second guide.

With all alignment degrees of freedom set, pins 525 are inserted into the distal femur 1 and through apertures 109, 111 (FIG. 26). These pins 525 serve to create holes 40 in the distal femur which will set the rotation of the implant through subsequent steps in the TKA surgical technique. These pins 525 also serve to further stabilize the guide 500.

Figure 27:
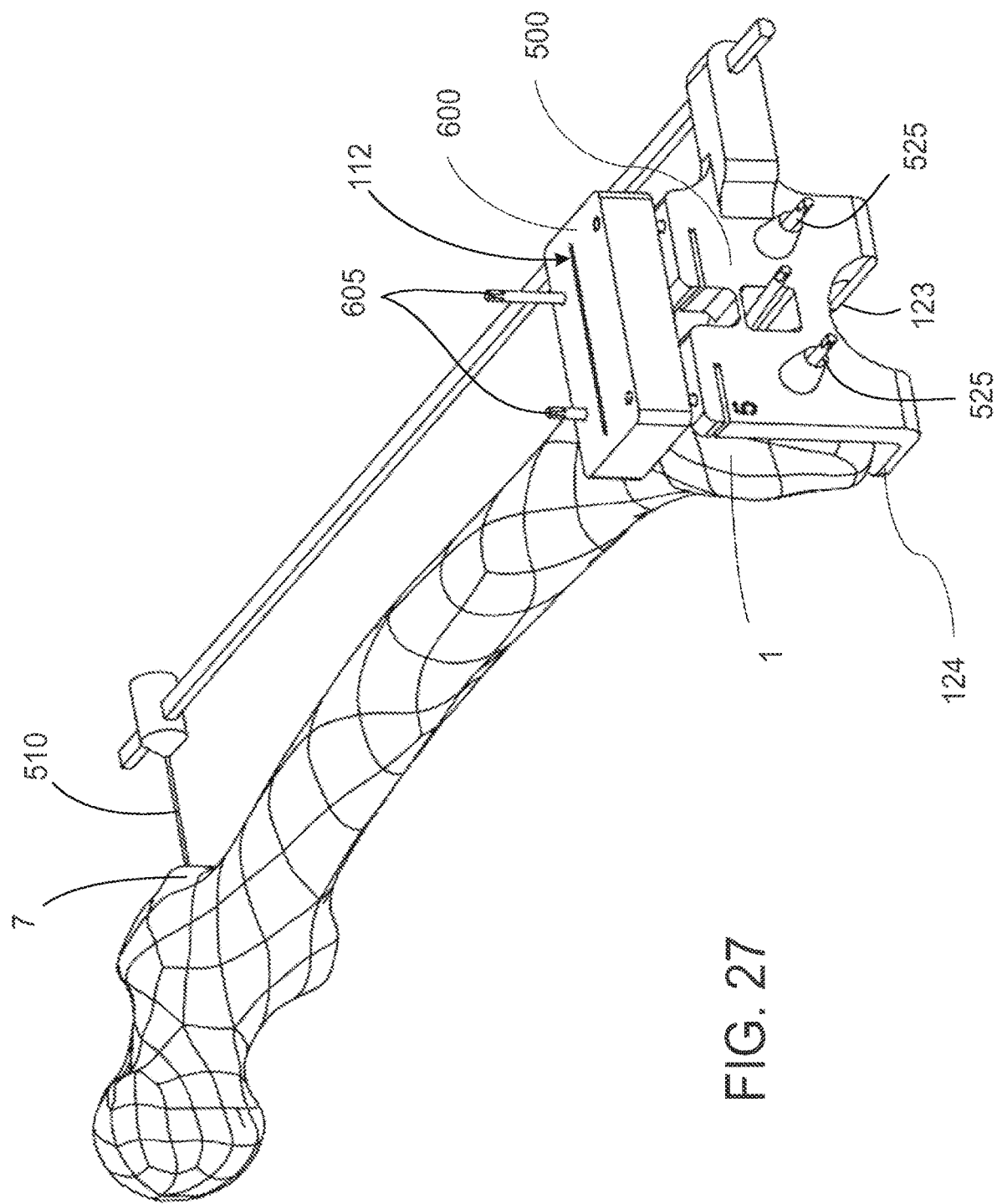

Next, as shown in FIGS. 26 and 27, a second guide 600 is attached to the guide 500. The second guide 600 could be constructed as a single piece with guide 500. The second guide 600 serves to guide additional pins 605 using apertures 601 and could also guide a saw in the making of a resection through an elongated resection aperture 112. This resection could be a distal resection or an anterior resection depending on how the second guide 600 is preoperatively configured to connect with the guide 500. The second guide 600 mates with the guide 500 such that the elongated resection aperture 112 and additional pin apertures 601 are located at a preoperatively selected offset from the preoperatively selected resection reference.

With guide 500 secured to the distal femur 1 by pins 525 through apertures 109, 111, the second guide 600 mated to the guide 500 and secured to the distal femur 1 by pins 605 through apertures 601, the assembly, the resection can now be made through the elongated resection aperture 112. Prior to making the resection, the surgeon may opt to disassemble some or all the assembly except for the pins 605 and second guide 600. Alternatively, the surgeon may elect to forgo the use of the second guide 600 and instead elect to assemble an alternative guide to pins 605.

With the femoral implant alignment guide 100 in an appropriate location relative to the femur 1, a saw or other cutting device may be used to remove at least a portion of the femoral condyles along the plane defined by the elongated resection aperture 112, which is illustrated in FIGS. 3B, 5-7, and 9. Depending upon the configuration of the femoral component, other cuts to the femur may be necessary prior to implantation of the femoral component. Also, in some embodiments, an extension measurement may result in recognition of the need for an additional femoral cut. If this happens, an additional cut through the femoral implant alignment guide 100 or separate from the femoral implant alignment guide 100 may be necessary to ensure proper fit of the arthroplasty device.

In an additional act of the method, the tibial implant alignment guide 300, as illustrated in FIG. 12, is provided to assist with aligning the tibial component of the knee arthroplasty device by making an appropriate cut on the tibia 2. The tibial implant alignment guide 300 includes a distal femur gauge including medial and lateral condyle paddles 312, 314. These condyle paddles 312, 314 along with the interface pins 340, which are configured to couple with connection holes 40 in the femur 1, provide an interface with the patient's femur, such as the femur 1 illustrated in FIG. 11. Other devices and techniques for aligning and coupling the tibial implant alignment guide 300 with the patient's femur 1 may be effective as well. For example, an alternative embodiment for a tibial alignment guide is illustrated in use in FIG. 16B. This alternative embodiment typical alignment guide does not include an integrated component that provides a guide for resection of the tibia 2. However, it is useful in achieving alignment of the tibia 2 and the femur 1.

In a further act of this method embodiment, the patient's tibia 2 is appropriately positioned relative to the patient's femur 1. An appropriate positioning provides for recovered or corrected anatomical alignment of the patient. An additional consideration is the balancing of soft tissues adjacent to the knee joint such that the joint operates with even pressures and wear to the implant components. For the tibial implant alignment guide 300 illustrated in FIG. 12, the condyle paddles 312, 314 and their connecting components may be separated from the lower portion of the instrument such that after an alignment is accomplished with the patient's leg extended, the patient's leg may be flexed prior to cutting of the tibia 2. When aligning and positioning is complete a portion of the patient's tibia can be removed with a saw or other cutting device such that the tibia 2 is configured to receive a tibial component of the knee arthroplasty device. To complete some embodiments of the invention a femoral component, such as the femoral component 200 of the knee arthroplasty device, is implanted, and a tibial component is implanted.

Figure 18:
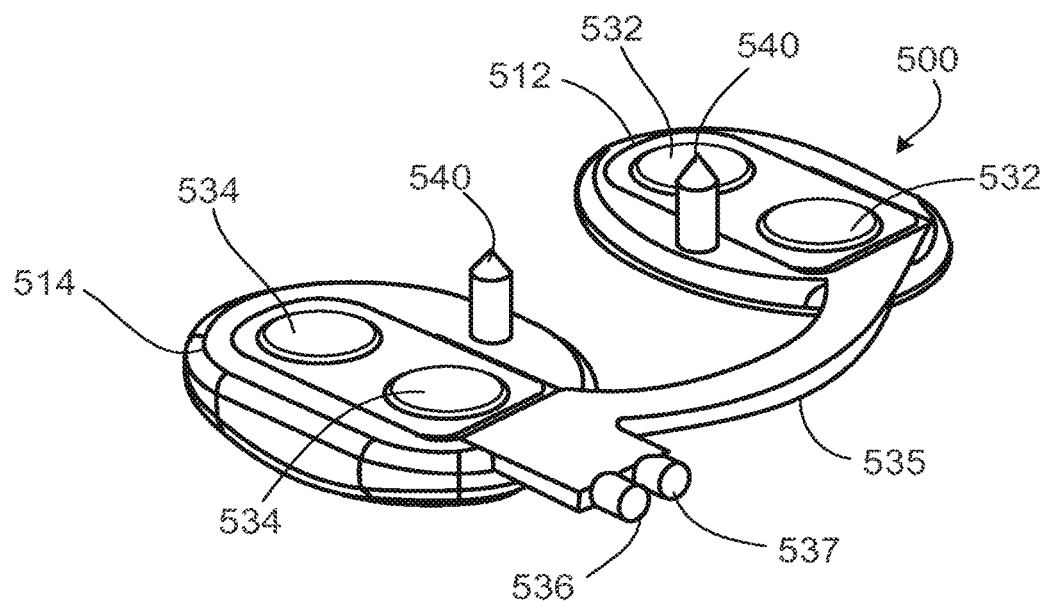
FIG. 18 is a perspective view of an instrument that includes a sensor.
Figure 19:
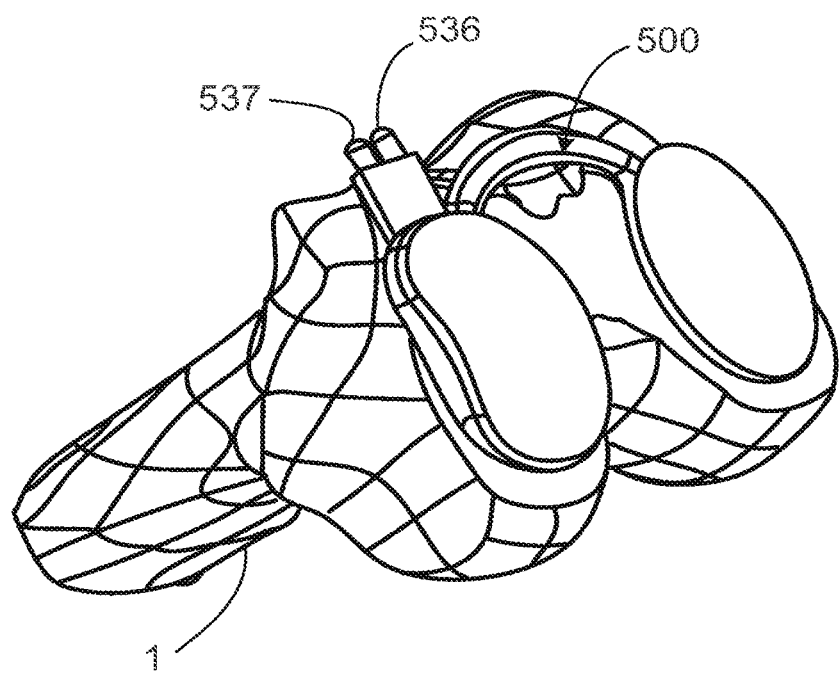
FIG. 19 is a perspective view of a distal portion of a femur to which an instrument of FIG. 18 has been coupled.

A patient-matched instrument with sensor 500 is illustrated in FIGS. 18-19. This patient-matched instrument with sensor 500 is similar in function to the distal femur gauge portion of the tibial implant alignment guide 300 illustrated in FIG. 15A, but includes additional sensor technology. The patient-matched instrument with sensor 500 is shown coupled to the distal end of the femur 1 in FIG. 19. The patient-matched instrument with sensor 500 includes medial and lateral condyle paddles 512, 514, each having a shape and size corresponding to a pre-operative planned distal resection of a patient's femur. Interface pins 540 that are configured to couple with connection holes 40 (FIG. 11) are also depicted. The condyle paddles 512, 514 are connected by a bridge 535. In various embodiments, these condyle paddles 512, 514 may be modular such that different shapes and sizes and different sensors may be substituted at either location. As illustrated, each of the condyle paddles 512, 514 includes a respective sensor 532, 534. The sensors may, without limitation, be pressure sensitive, measure location, or be sensitive to relative displacement. A first indicator light 536 and the second indicator light 537 are connected directly or through a logic circuit to one or both of the sensors 532, 534. In response to readings taken from the first indicator light 536 and the second indicator light 537, a user can more readily make decisions regarding placement and orientation of bone manipulations made in preparation for implanting an orthopedic device.

Indicator lights communicate force and/or balance and/or force location information using visible or invisible means. When using visible means, this information is communicated directly to the usual visually. When using invisible means, this information is communicated through an interpretive device which can perform translation, display, storage, and transmission tasks or merge the information with other data prior to performing the aforementioned tasks.

Figure 16B:
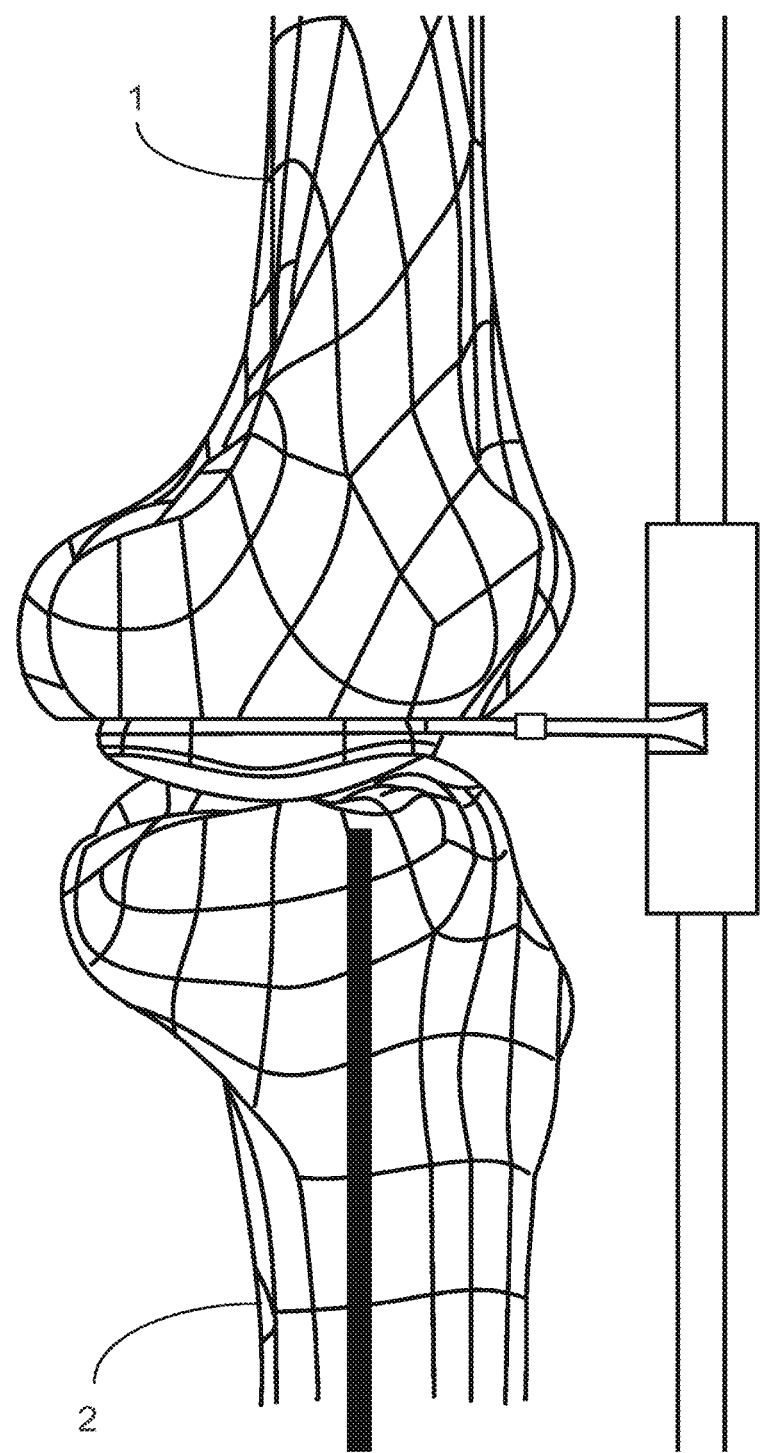
FIG. 16B is a side elevation view of a portion of a tibial implant alignment guide between a tibia and a femur in full terminal extension.

A method embodiment includes providing information useful for implanting an orthopedic implant by providing a patient-matched instrument that includes a sensor for measuring force applied to the patient-matched instrument. For example, the patient matched instrument with sensor 500 may include a sensor for measuring force in one or both of the sensors 532, 534. As shown in FIG. 19 the patient matched instrument with sensor 500 may be placed on the femur 1 where it can be placed between the femur 1 and another bone, an orthopedic instrument, or an orthopedic implant component (FIG. 16B). With the sensors 532, 534 in place as illustrated a method may include reading forces applied during alignment of two or more orthopedic instruments, orthopedic implant components, and bones. Once force readings are available, and possibly displayed through the indicator lights 536, 537, a user may accept the measured forces or may alter one or more of the orthopedic instruments, orthopedic implant components, and bones or other tissue to change the measured forces.

Figure 15E:
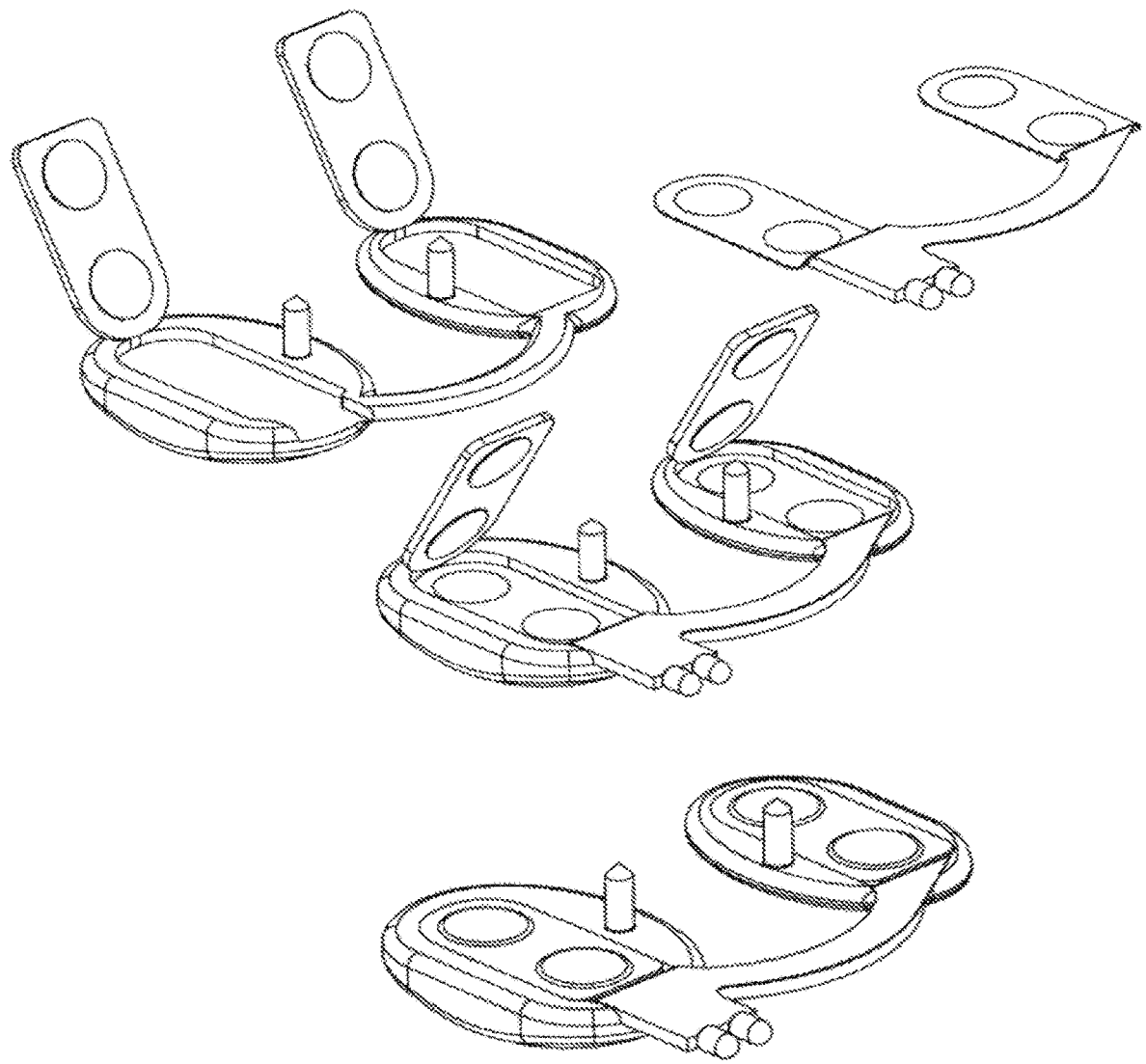
FIG. 15E is a series of views of an alternative embodiment of the instrument of FIG. 15A and a portable force sensor and output display.
Figure 16C:
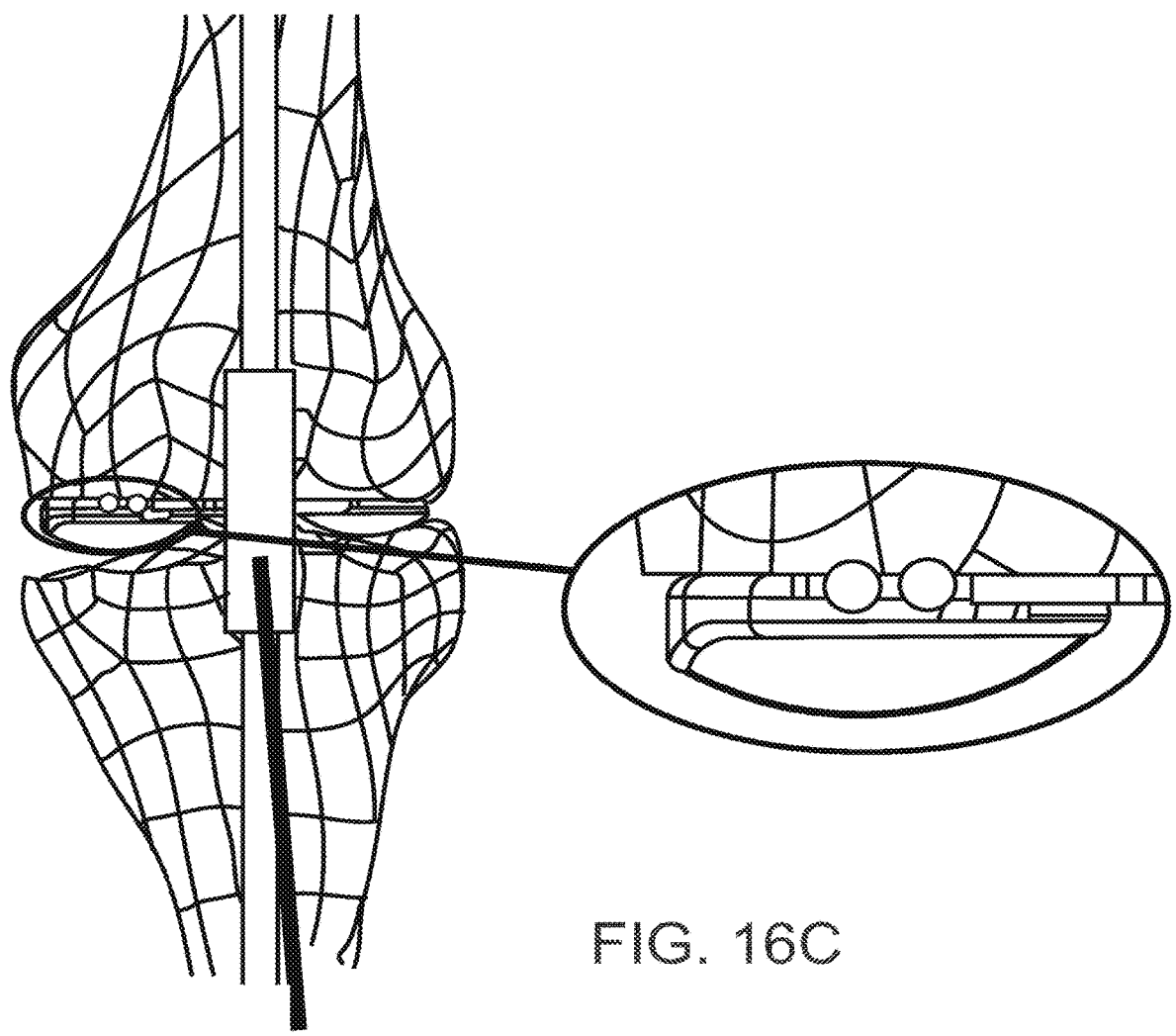
FIG. 16C is a frontal elevation view of the instrument of FIG. 16B between a tibia and femur where the tibia is coronally misaligned and illustrates the establishment of a patient-specific load and balance datum.
Figure 16D:
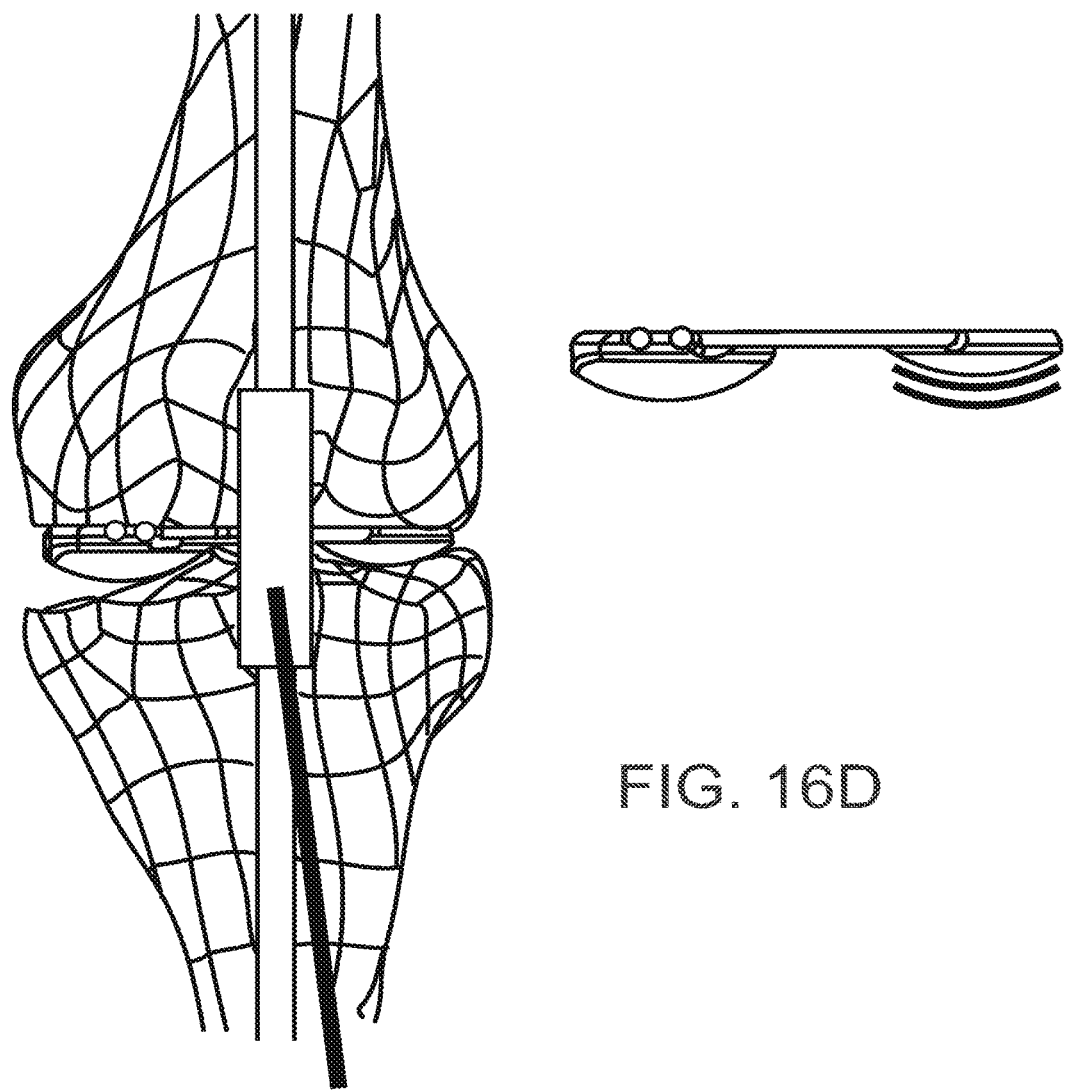
FIG. 16D is a frontal elevation view of the instrument of FIG. 16B between a tibia and femur where the tibia is coronally aligned after an alteration of the instrument shape.
Figure 16E:
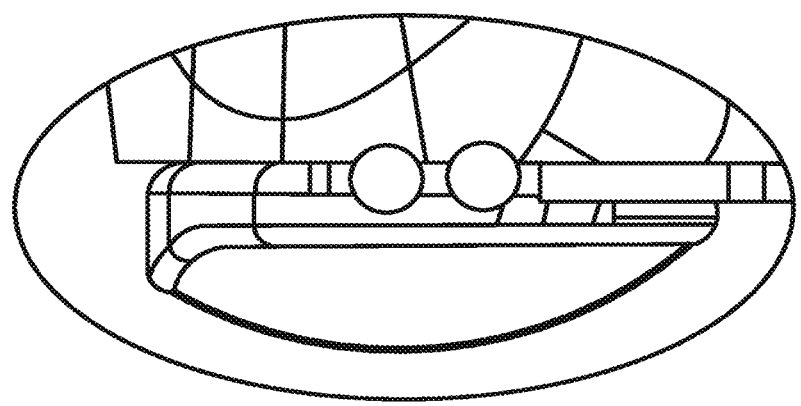
FIG. 16E illustrates a detected load and balance change relative to the patient-specific load and balance datum.
Figure 17:
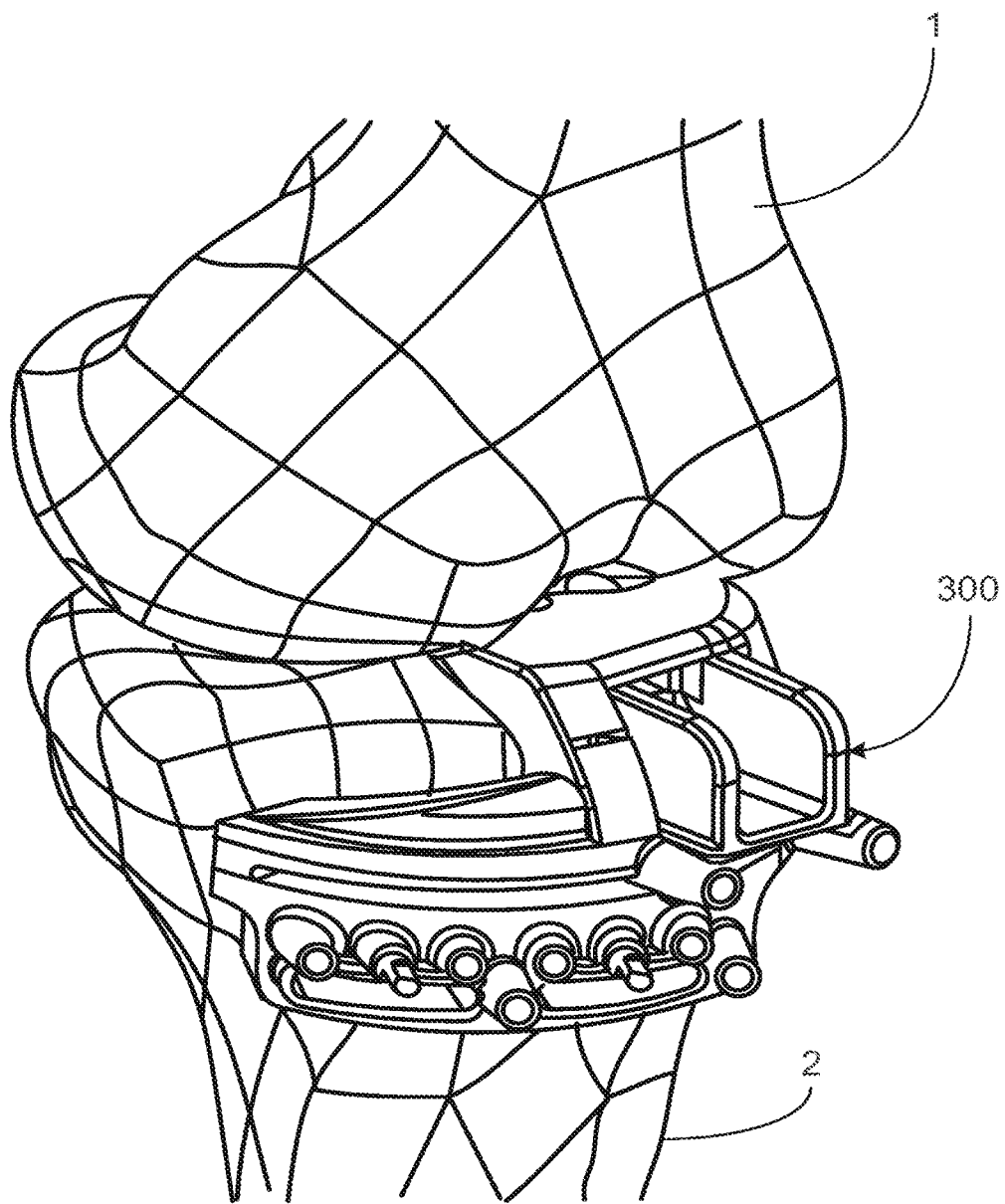
FIG. 17 is a perspective view of a tibial implant alignment guide between a tibia and a femur in full extension.

Another method embodiment includes indicator lights which can be zeroed or normalized to particular conditions for the purpose of comparing the effect of a relative change. For instance, beginning with a tibial guide configured to match the resected portions of the native distal femur condyles, the native forces and balance in extension would be restored and captured qualitatively or quantitatively through the aforementioned sensors imbedded within the "native" tibial guide. Native alignment would also be restored including any deformities in the coronal or sagittal planes (FIG. 16C). At this time, the sensors and/or indicator lights can be zeroed relative to the "native" condition of the knee in extension as reproduced by the unaltered replica of the native distal femur (FIG. 16C). Next, the tibia guide and/or distal femur resection can be reconfigured through a variety of means (FIGS. 15B-15D) to correct for any sagittal or coronal alignment deformities (FIG. 16D), including a transfer of the sensor from the native replica shape to the corrected replica shape as shown in FIG. 15E. The changed involved would benefit alignment at the cost of extension forces and balance (FIG. 16E, indicating an imbalance). Typically this negative effect on forces and balance is not precisely detectable to the surgeon but only roughly detectable through tactile perception or spacer shims. With the use of sensors and indicators calibrated to detect the effect of the change in alignment, now the effect of alignment improvements on soft tissue generated forces and balance can be precisely measured, evaluated and accounted for through informed subsequent surgical action. This calibration, or zeroing of sensors relative to a patient-specific "force datum" alleviates at least one common problem type in TKA: the variable effect of upper and lower limb weight on the tactile evaluation of knee forces and balance.

Force or balance deltas with respect to the patient-specific force datum can be communicated to the user directly through visual indicators or indirectly through either indicators visible or invisible to the surgeon, which can be detected by an interpretive device. This interpretive device can perform translation, display, storage or transmission tasks or merge the two or more data sets prior to performing the aforementioned tasks. Such an interpretive device can also be equipped to visually detect the alignment of the tibia through the use of fiducial makers present on an alignment rod and the tibia. Such markers on the tibia can be ink marks made by the surgeon indicating anatomic landmarks or can be features of an instrument placed by the surgeon on anatomic landmarks of the tibia. By detecting both force and alignment information, the interpretive device is enabled to provide a greater variety of output to the surgeon through translation, display, storage, transmission or merging two or more data sets prior to the aforementioned tasks. By combining two or more data sets, the interpretive device may allow for more a simplification of beneficial yet complex intraoperative decision making. For instance the use of multiple patient matched instruments coupled with sensors calibrated to patient-specific "force datums" are considered where each instance is applied to one of several articulating compartments of the knee joint including the distal femur and proximal tibia, the posterior femur and proximal tibia, the anterior femur and posterior patella. With more than one input to consider, the interpretive device could bear the burden of translating inputs to decisions or recommendations through logical programming.

Figure 22A:
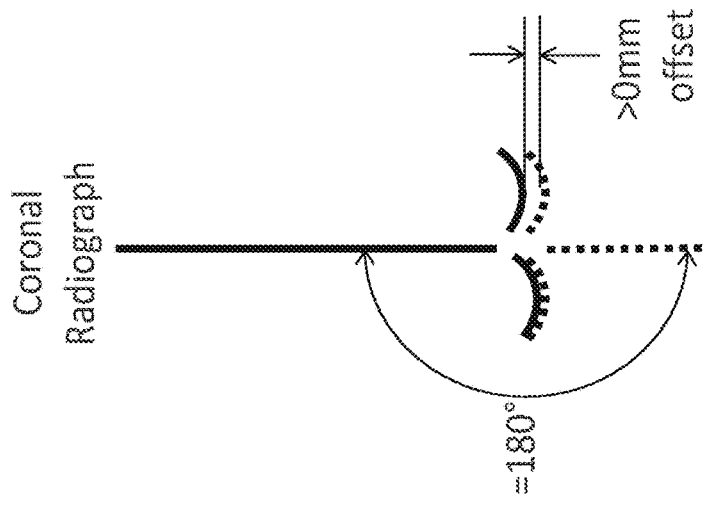
FIGS. 22A-22C are a series of coronal radiographs showing undeformed alignment, deformed alignment, and restored alignment.
Figure 22B:
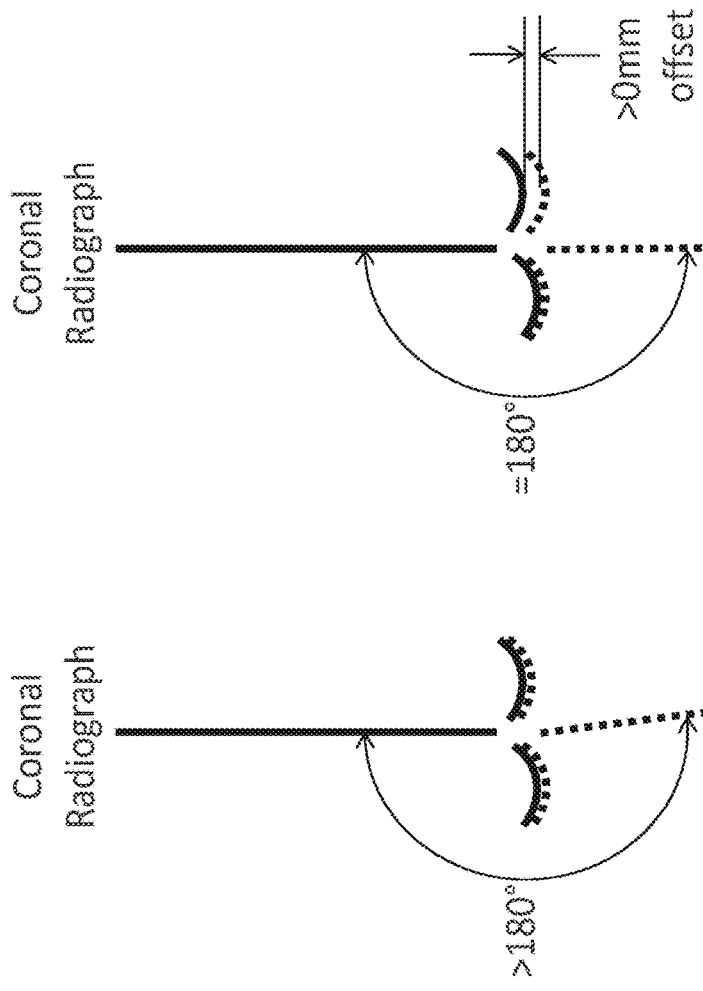
Figure 22C:
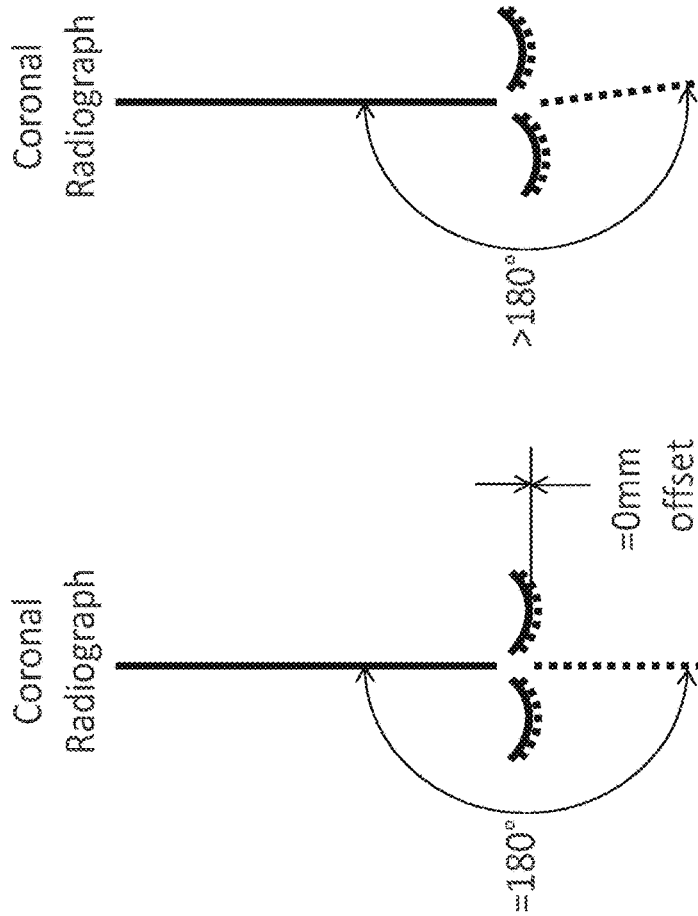

As illustrated in FIGS. 15B-15D, the tibia guide can be reconfigured by applying offsets to the replica(s), and the reconfigured replica(s) can be made modular to allow for intraoperative changes or there could be a family of single piece constructs. One or more reconfigured replica options can be provided to the surgeon for intraoperative assessment and final decision making. These reconfigured replica options can be designed utilizing patient deformity information (FIG. 22B) acquired from full femur and tibia radiographs taken in substantially medial-lateral and/or anterior-posterior orientation and/or from functional assessment by the surgeon in preoperative consultation such as maximum passive flexion/extension, coronal laxity, or anterior/posterior drawer testing. FIG. 22A illustrates an undeformed alignment where a reconfigured replica is not needed; FIG. 22B illustrates a deformed alignment; and FIG. 22C illustrates restored alignment of the femur and tibia of FIG. 22B using a reconfigured replica.

Implants can be manufactured and provided intraoperatively, which reflect the geometry of the reconfigured replicas. The implants can be designed or selected to optimally address the particular deformity which necessitated the particular reconfigured replica.

Alternative embodiments of the process of using a patient-matched instrument coupled with a sensor or establishing and using a patient-specific "force datum" described above for the medial and/or lateral tibia-femoral compartments in extension include applications of the same device or process for the medial and/or lateral tibia-femoral compartments in particular or all degrees of flexion and extension including removing and replacing distal and posterior femur condyles or proximal tibia condyles, and also for the patella-femoral (PFJ) compartment in particular or in all degrees of flexion and extension including removing and replacing the anterior femur or posterior patellar anatomy. Application of the process of establishing and using a patient-matched instrument coupled with sensors or a patient-specific "force datum" is considered for each of the aforementioned compartments and anatomies individually or in combination of two or more compartments and/or anatomies.

Figure 20:
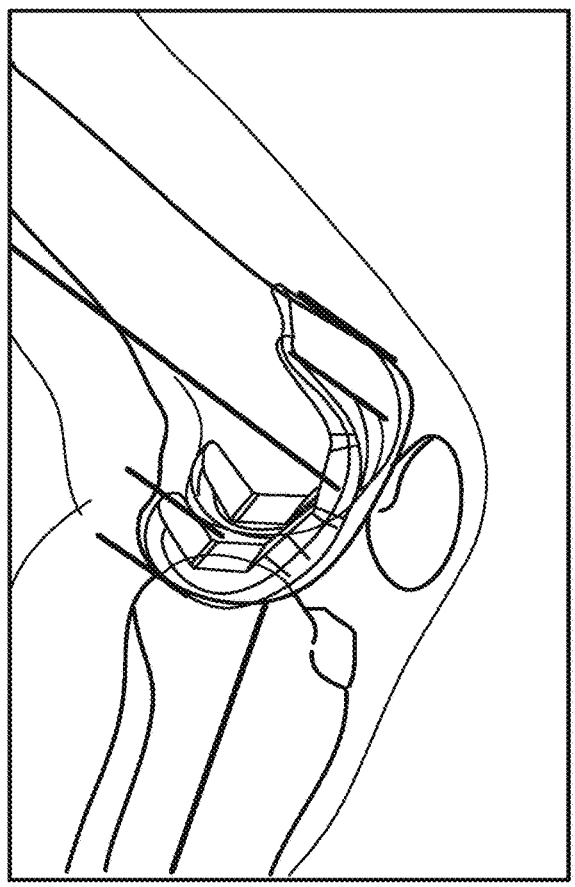
FIG. 20 is a frontal elevation view of a preoperative radiograph having an aligned representation of the femoral implant overlaid in preparation for comparison with the postoperative radiograph of the implanted femoral implant.
Figure 21:
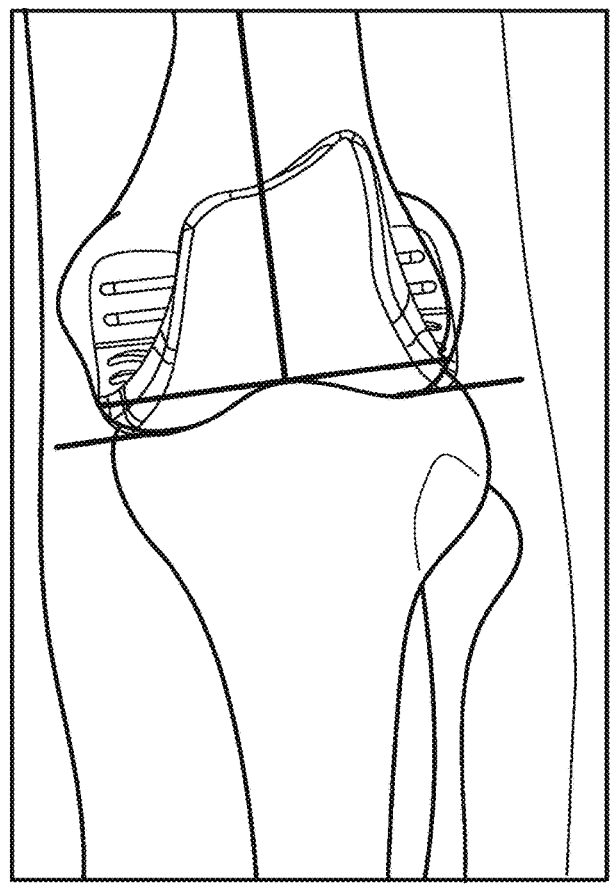
FIG. 21 is a sagittal elevation view of a preoperative radiograph having an aligned representation of the femoral implant overlaid in preparation for comparison with the postoperative radiograph of the implanted femoral implant.

FIGS. 20 and 21 illustrate preoperative plan information, including the information related to the design of the PM instrument and the planned implant placement, provided to the surgeon in the context of preoperative radiographs. To acquire some types of preoperative information needed to correctly visually express the planned alignment, two or more radiographs may be required to allow triangulated points, axes and planes derived from landmarks of the bone to serve as references for aligning points, axes and planes of the implant. The two radiographs can be taken, for example, with the patient placed in differing orientations, particularly with at least some flexion and rotation differences between radiographs. At least one preoperative radiograph can be configured for viewing intraoperatively for reference and post-operatively for comparison with a postoperative radiograph using conventional radiograph viewing means such as a light box. Preoperative radiographs can be configured for overlay comparison with postoperative radiographs such that the preoperative plan information and the postoperative result information can be directly visually compared using conventional radiograph viewing means. Such direct visual overlay comparison assumes that the patient is oriented relative to the x-ray emitter in a way substantially consistent between preoperative and postoperative radiographs. In the case when the patient is not consistently rotated in preoperative and postoperative radiographs, more than one postoperative radiograph can be acquired to allow for triangulation of points, axes and planes derived from landmarks of the implant and bone, which provide the ability to quantify the orientation or transformation between the preoperative and postoperative implants and bones. To facilitate the comparison of preoperative and postoperative implant to bone alignment, several approaches can be taken. One approach takes separate radiographs of the full femur and full tibia to ensure each is oriented to the x-ray emitter consistently between preoperative and postoperative radiographs. A second approach constrains the femur, tibia or full leg with an anatomical brace either having a known orientation relative to the x-ray emitter or having fiducial markers of a known fixed relationship to the patient-constraining features of the brace. Such a brace constrains or provides references for the heel to toe axis and location, the hip to hip axis and location, and the ground to tibia angle to ensure consistent body placement when planning or evaluating alignment of implants. The capability of the preoperative plan to predict postoperative results can be enhanced with additional radiographs of differing yet known orientations.

Quantified preoperative and postoperative alignment comparisons can be provided to a customer for purposes of tracking the amount of variation which exists across the span of the TKA process steps (preoperative measurement, planning, design, manufacture, intraoperative alignment, balance and postoperative measurement). Such data can be delivered to the customer in a format conducive to demonstrating process control or quantifying process noise, particularly in a manner where postoperative measurements are described in terms of their deviation from preoperative planning targets. Such preoperative to postoperative radiographic comparison feedback data can be provided to the surgeon in a variety of formats at regular intervals and could be coupled with preoperative and postoperative physiological data, active or passive stability, balance, function, motion and pain data acquired during postoperative rehabilitation, other historical data from the patient or a pool of patients. Such a system of feedback loops can serve as a basis for recommendations for improvements to preoperative planning and design, intraoperative balance and postoperative rehabilitation steps in the span of the TKA process.

Such a system of feedback loops can be particularly useful for educating decisions made in preoperatively planning and intraoperative balance steps. For example, when preoperatively planning, a surgeon can adjust pre-operative alignment targets, designs or intraoperative force or balance deltas with respect to the patient-specific force datum based on the effect of alignment target on rehab metrics. For another example, preoperative planning, intraoperative balancing or postoperative rehab protocols can be adjusted to account for particular preoperative qualities for the purpose of minimizing the potential of adverse rehab metrics. Long term outcome metrics such as survivorship and patient satisfaction can be coupled to further educate decisions made during steps in the span of the TKA process.

Feedback loops can exist both between surgeries and within a surgery. Feedback loops within surgery described herein include those related to the balance and alignment of the knee joint through the use of a patient matched instrument coupled with a sensor and indicators capable of establishing a patient specific force datum and providing information regarding the effect of alignment changes with respect to that force datum. This feedback loop can be enhanced using an interpretive device intraoperatively. In such cases, the interpretive device can facilitate not only the intraoperative feedback loop but also an interoperative (between surgeries) feedback loop by incorporating external data to inform intraoperative balance and alignment decision criteria.

Various embodiments of a surgical instrument wholly or its components individually may be made from any biocompatible material. For example and without limitation, biocompatible materials may include in whole or in part: non-reinforced polymers, reinforced polymers, metals, ceramics and combinations of these materials. Reinforcing of polymers may be accomplished with carbon, metal, or glass or any other effective material. Examples of biocompatible polymer materials include polyamide base resins, polyethylene, low density polyethylene, polymethylmethacrylate (PMMA), polyetheretherketone (PEEK), polyetherketoneketone (PEKK), a polymeric hydroxyethylmethacrylate (PHEMA), and polyurethane, any of which may be reinforced. Example biocompatible metals include stainless steel and other steel alloys, cobalt chrome alloys, tantalum, titanium, titanium alloys, titanium-nickel alloys such as Nitinol and other superelastic or shape-memory metal alloys.

Terms such as distal, proximal, medial, lateral, and the like have been used relatively herein. However, such terms are not limited to specific coordinate orientations, but are used to describe relative positions referencing particular embodiments. Such terms are not generally limiting to the scope of the claims made herein. Any embodiment or feature of any section, portion, or any other component shown or particularly described in relation to various embodiments of similar sections, portions, or components herein may be interchangeably applied to any other similar embodiment or feature shown or described herein.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the invention should not be limited by any of the above-described exemplary embodiments, but should be defined only in accordance with the claims and their equivalents.

What is claimed is:

1. A method of manufacturing a femoral implant alignment guide, the method comprising:
    obtaining one or more images of anatomy of a patient that include at least a hip and a knee of the patient;
    evaluating the one or more images to define an axis from between femoral condyles of a distal portion of a femur of the patient through a hip center of the patient;
    forming a patient-matched body based on the defined axis, wherein the patient-matched body comprises:
        a first elongated resection aperture that when placed against the femoral condyles has a major axis that is substantially perpendicular to the defined axis when the patient-matched body is aligned with respect to the defined axis, is configured to receive a cutting tool, and defines a plane of resection of the femoral condyles; and
        an offset portion that has a first rod aperture and a second axis in a coronal plane of the patient, and substantially parallel to the major axis, and is configured to extend at least to a point in the coronal plane that is shared with a greater trochanter of the patient when the patient-matched body is aligned with respect to the defined axis;
    forming a rod, wherein the first rod aperture is configured to receive a first portion of the rod; and
    forming a proximal trochanter probe comprising:
        a second rod aperture configured to receive a second portion of the rod; and
        a tip configured to be inserted into the patient until contact with a most lateral point of the greater trochanter when the first and second portions of the rod are received by the first and second rod apertures, respectively.

2. The method of claim 1, further comprising forming medial and lateral contact surfaces in the patient-matched body, wherein the medial and lateral contact surfaces are configured to contact medial and lateral condyles, respectively, of the femoral condyles when the patient-matched body is coupled to the distal portion of the femur.

3. The method of claim 2, wherein the one or more images comprise at least one medial-lateral or anterior-posterior radiograph of the knee, and wherein the method further comprises
    analyzing the at least one medial-lateral or anterior-posterior radiograph to identify one or more markers indicating one or more locations of one or more physiological reference points on the distal portion of the femur comprising medial or lateral distal femur condyle points, a medial anterior ridge, a lateral anterior ridge, or a medial or lateral posterior condyle; and
    correlating one or more of a size or a shape of one or more of the medial or lateral contact surfaces with one or more of the identified markers when forming the one or more of the medial or lateral contact surfaces.

4. The method of claim 2, further comprising:
    evaluating the one or more images to define a distal mechanical point of the femur in the coronal plane; and
    forming a first tab on a medial portion of the medial contact surface and a second tab on a lateral portion of the lateral contact surface, wherein the first and second tabs are configured to constrain a relationship between the patient-matched body and the defined distal mechanical point.

5. The method of claim 1, further comprising forming a cylindrical bore in the offset portion in order to form the first rod aperture, wherein the cylindrical bore is configured to constrain the rod in the coronal plane.

6. The method of claim 1, further comprising forming a slot in the offset portion in order to form the first rod aperture, wherein the slot is configured to allow translation of the rod when the first portion of the rod is received by the first rod aperture.

7. The method of claim 1, further comprising:
    evaluating the one or more images to define proximal and distal mechanical points of the femur in the coronal plane;
    determining a distance between the defined proximal and distal mechanical points; and
    forming the rod to have a length determined based on the distance.

8. The method of claim 1, further comprising evaluating the one or more images to define the most lateral point of the greater trochanter, wherein the tip comprises a length determined based on the defined most lateral point of the greater trochanter and an interface with the rod.

9. The method of claim 1, further comprising forming the first and second rod apertures to have a shape configured to restrict rotation of the rod about a long axis of the rod when the first and second portions of the rod are received by the first and second rod apertures, respectively, wherein the rod comprises a cross-section corresponding to the shape.

10. A method of manufacturing a femoral implant alignment guide, the method comprising:
obtaining one or more of a medial-lateral or an anterior-posterior radiograph of anatomy of a patient, wherein the anatomy includes at least a hip and a knee of the patient;
evaluating the one or more of the medial-lateral or anterior-posterior radiographs to define an axis from between femoral condyles of a distal portion of a femur of the patient through the hip center of the patient and identify one or more markers indicating one or more locations of one or more physiological reference points on the distal portion of the femur;
forming a patient-matched body based on the defined axis and the identified one or more markers, wherein the patient-matched body comprises:
medial and lateral contact surfaces comprising one or more of a size or a shape determined based on the identified one or more markers and configured to contact medial and lateral condyles, respectively, of the femoral condyles when the patient-matched body is coupled to the distal portion of the femur;
a first elongated resection aperture having a major axis that is substantially perpendicular to the defined axis when the patient-matched body is aligned with respect to the defined axis; and
an offset portion that has a first rod aperture and a second axis in a coronal plane of the patient, and substantially parallel to the major axis, and is configured to extend at least to a point in the coronal plane that is directly lateral a greater trochanter of the patient when the patient-matched body is aligned with respect to the defined axis;
forming a rod, wherein the first rod aperture is configured to receive a first portion of the rod; and
forming a proximal trochanter probe comprising:
a second rod aperture configured to receive a second portion of the rod; and
a tip configured to be inserted into the patient until contact with a most lateral point of the greater trochanter when the first and second portions of the rod are received by the first and second rod apertures, respectively.

11. The method of claim 10, further comprising determining a distance between proximal and distal mechanical points of the femur in the coronal plane, wherein the rod comprises a length determined based on the distance.

12. The method of claim 10, further comprising forming a cylindrical bore or a slot in the offset portion in order to form the first rod aperture.

13. The method of claim 10, wherein the tip comprises a length determined based on the most lateral point of the greater trochanter and an interface with the rod.

14. The method of claim 10, further comprising defining the first and second rod apertures to have a shape configured to restrict rotation of the rod about a long axis of the rod when the rod is received by the first and second rod apertures.

15. The method of claim 10, further comprising forming at least one of a first tab on a medial portion of the medial contact surface or a second tab on a lateral portion of the lateral contact surface, wherein the first and second tabs are configured to constrain a relationship between the patient-matched body and a distal mechanical point of the femur in the coronal plane.

16. A method of manufacturing a femoral implant alignment guide, the method comprising:
defining an axis from between femoral condyles of a distal portion of a femur of a patient through a hip center of the patient, and proximal and distal mechanical points of the femur in a coronal plane of the patient, based on one or more obtained images of the patient;
forming a rod comprising a length determined based on a determined distance between the defined proximal and distal mechanical points;
forming a patient-matched body based on the defined axis, wherein the patient-matched body comprises a first elongated resection aperture having a major axis that is substantially perpendicular to the defined axis when the patient-matched body is aligned with respect to the defined axis and an offset portion that has a first rod aperture configured to receive the rod and a second axis in a coronal plane of the patient, and substantially parallel to the major axis, and is configured to extend at least to a point in the coronal plane that is lateral a greater trochanter of the patient when the patient-matched body is aligned with respect to the defined axis; and
identifying a most lateral point of the greater trochanter in one or more of the obtained images and forming a proximal trochanter probe comprising a second rod aperture configured to receive the rod and a tip comprising a length determined based on the most lateral point of the greater trochanter and an interface with the rod.

17. The method of claim 16, further comprising:
analyzing one or more of the obtained images to identify one or more markers indicating one or more locations of one or more physiological reference points on the distal portion of the femur; and
forming medial and lateral contact surfaces on the patient-matched body to have one or more of a size or a shape based on the identified markers, wherein the medial and lateral contact surfaces are configured to contact medial and lateral condyles, respectively, of the femoral condyles when the patient-matched body is coupled to the distal portion of the femur.

* * * * *